(12) United States Patent
Liang et al.

(10) Patent No.: US 6,329,504 B1
(45) Date of Patent: Dec. 11, 2001

(54) ANTIFUNGAL POLYPEPTIDE AND METHODS FOR CONTROLLING PLANT PATHOGENIC FUNGI

(75) Inventors: Jihong Liang; Dilip Maganlal Shah, both of Chesterfield; Yonnie S. Wu, Wildwood; Cindy A. Rosenberger, Ballwin; Salim Hakimi, Chesterfield, all of MO (US)

(73) Assignee: Monsanto Company, St. Louis, MD (US)

( * ) Notice: Subject to any disclaimer, the term of this patent is extended or adjusted under 35 U.S.C. 154(b) by 0 days.

(21) Appl. No.: 09/428,805

(22) Filed: Oct. 28, 1999

Related U.S. Application Data

(62) Division of application No. 08/766,355, filed on Dec. 13, 1996, now Pat. No. 6,121,436.

(51) Int. Cl.[7] .............................. A01G 13/00; C07K 7/00; C07H 21/00; C12P 21/00; A61K 35/78
(52) U.S. Cl. .......................... 530/350; 530/325; 530/326; 530/324; 435/69.1; 435/70.1; 435/172.3; 435/418; 435/419; 536/23.1; 536/23.6; 514/2; 514/12; 514/19; 800/205; 800/200
(58) Field of Search .............................. 800/205; 530/350, 530/325; 435/69.1, 172.3, 70.1, 419, 418; 536/23.6; 514/12, 2, 19

(56) References Cited

U.S. PATENT DOCUMENTS 5,530,187   6/1996   Lamb et al. ................... 800/205

FOREIGN PATENT DOCUMENTS

| 460753 A2 | 12/1991 | (EP) | ................ 15/29 |
| WO 94/16076 | 7/1994 | (WO) | ................ 15/29 |
| 94/16076 * | 7/1994 | (WO) . | |

OTHER PUBLICATIONS

Ishibashi et al., "Stored mRNA in cotyledons of *Vigna unguiculata* seeds: nucleotide sequence of cloned cDNA for a stored mRNA and induction of its synthesis by precocious germination," vol. 15, pp. 59–64, 1990.
International Search Report dated May 20, 1998.

* cited by examiner

*Primary Examiner*—Christopher S. F. Low
*Assistant Examiner*—Chih-Min Kam
(74) *Attorney, Agent, or Firm*—TK Ball, Esq.; Howrey Simon Arnold & White

(57) ABSTRACT

Antifungal polypeptides, isolated from Medicago plants, are shown to control fungal damage to plants. DNA encoding the polypeptides was cloned into vectors for transformation of plant-colonizing microorganisms or plants, thereby providing a method of inhibiting fungal growth on plants. The polypeptides can be formulated into compositions useful in controlling undesired fungi.

7 Claims, 10 Drawing Sheets

TGTCAAACACACATAACACATAAGTGACCGTGAGTCATTAAATTTATATATTCATCAATC

Figure 4:
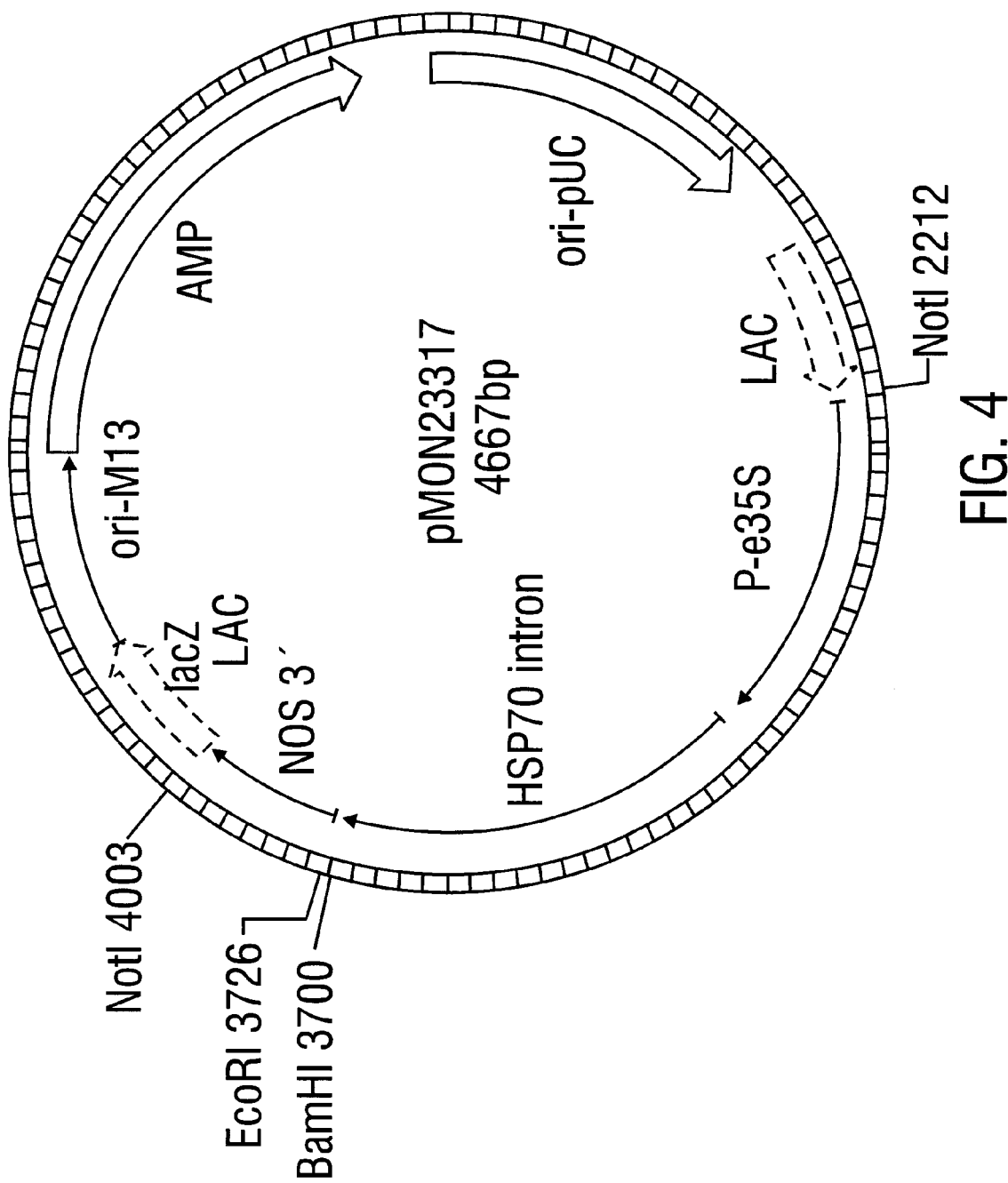

TAATCAAACTATGGAGAAGAAATCACTAGCTGGCTTATGCTTCCTCTTCTTGGTTCTCTTTGTT
          M   E   K   K   S   L   A   G   L   C   F   L   F   L   V   L   F   V

GCACAAGAAATTGTGGTTGACAGAAGCCAGAGAATTTGAGAATTTGGCAGATAAATATAGGGGAC
 A   Q   E   I   V   V   T   E   A   R   T   C   E   N   L   A   D   K   Y   R   G   P

CATGCTTTAGTGGGTGTGACACTCACTGCACACAACCAAAGAGAACGCAGTTAGTGGAAGGTGTAG
 C   F   S   G   C   D   T   H   C   T   T   K   E   N   A   V   S   G   R   C   R

GGACGACTTCCGCTGCTGGTGTACTAAAAGATGTTAAATGGATCTCCTCCAACATCAAGATGTG
 D   D   F   R   C   W   C   T   K   R   C   *

CATGGAATAGTCTTTATAATAAAACTAAATAAATGCACGCAGTATAGCTACAACTTCAT

CTATTATATGTACTCAATATCGNGCATAACGTATTAGTTATGCACTTCTATCATATGGAATAAA

CATAATAAGTAATTTCGTNTCCAAAAAAAAAAAAAAAA

FIG. 1

```
pI230    MEKKSLACLSFLLLVLFVAQEIVVSEANTCENLAGSYKGVCFGGCDRHCRTQEGAISGRCRDDFRCWCTKNC
         ||||||||||||||||||| ||| ||||||||||| |||||||||||||||||||||||||||||||||||
AlfAFP2  MEKKSLAGLCFLFLVLFVEQEIMVTEAATCENLANTYRGPCFGGCDFHCKTKEHLLSGRCRDDFRCCXXXXX
         ||||    |||| ||||| |||| || ||||||| | || |||||||| ||| |  |||||||||||
AlfAFP1  XXXXXXXGLCFLFLVLFVAQEIVVTEARTCENLADKYRGPCFSGCDTHCTTKENAVSGRCRDDFRCWCTKRC
         |||||||||| ||||||||||||||||||||||||||||||||||||||||| |||||||||||||||||
pI230    MEKKSLACLSFLLLVLFVAQEIVVSEANTCENLAGSYKGVCFGGCDRHCRTQEGAISGRCRDDFRCWCTKNC
```

FIG. 2

```
AlfAFP2  TGTCAAACACACACATAACACATAAGTGACCGTGAGTCATTAAATTTATA
AlfAFP1  --------------------------------------------------

AlfAFP2  TATATTCATCAATCTAATCAAACTATGGAGAGAAGAAATCACTAGCTGGCTTA
AlfAFP1  -----------------------------------------CTGGCTTA
                                                  *******

AlfAFP2  TGCTTCCTCTCCTCGTTCTCTCTTGTTGAACAAGAAATTATGGTGACCGAG
AlfAFP1  TGCTTCCTCTCTTGGTTCTCTTTGTTGCACAAGAAATTGTGGTGACAGAA
         *********** * *** **** **** *********** ***** **** **

AlfAFP2  GCAGCTACTTGTGTGAGAATTTGGCTAACACATACAGGGGACCATGCTTCGGT
AlfAFP1  GCCAGAACATGTGAGAATTTGGCAGATAAATATAGGGGACCATGCTTTAGT
         ** *  ** ************ * *** ** ************ * **

AlfAFP2  GGTTGTGACTTTCACTGCAAAACCAAAGAACACTTACTTAGCGGXAGGTGC
AlfAFP1  GGTTGTGACACTCACTGCACCAACCAAAGAGAACGCAGTTAGTGGAAGGTGT
         ********* ********  ** ****** **** ** ***** ** *****

AlfAFP2  AGGGACGACTTCCGCTGCTGCTGGATCC
AlfAFP1  AGGGACGACTTCCGCTGCTGCTGGATCC
         ****************************

FIG. 3
```

ANTIFUNGAL POLYPEPTIDE AND METHODS FOR CONTROLLING PLANT PATHOGENIC FUNGI

This is a divisional of co-pending application Ser. No. 08/766,355, Dec. 1, 1996.

BACKGROUND OF THE INVENTION

1. Field of the Invention

The present invention relates to antifungal polypeptides obtainable from plants in the genus Medicago, and methods for controlling pathogenic fungi employing the antifungal polypeptides. The antifungal polypeptides may be applied directly to a plant, applied to a plant in the form of microorganisms that produce the polypeptides, or the plants may be genetically modified to produce the polypeptides. The present invention also relates to DNA sequences, microorganisms and plants transformed with the DNA, and compositions useful in controlling pathogenic plant fungi.

2. Description of Related Art

Protection of agriculturally important crops from insect and disease has become a major concern in the industry. Fungus infection is a particular problem in damp climates and may become a major concern during crop storage. Plants have developed a certain degree of natural resistance to pathogenic fungi; however, modern growing methods, harvesting and storage systems frequently provide a favorable environment for plant pathogens.

Adding to the problem is the number of different fungi that may cause problems. Fungal damage can be caused by a fungus of genera such as Alternaria; Ascochyta; Botrytis; Cercospora; Colletotrichum; Diplodia; Erysiphe; Fusarium; Gaeumanomyces; Helminthosporium; Macrophomina; Nectria; Peronospora; Phoma; Phymatotrichum; Phytophthora; Plasmopara; Podosphaera; Puccinia; Pythium; Pyrenophora; Pyricularia; Rhizoctonia; Scerotium; Sclerotinia; Septoria; Thielaviopsis; Uncinula; Ventiiria; and Verticillium. Therefore, fungicidal compounds are not always effective because activity may be limited to a few species.

One approach to inhibiting plant pathogenic activity has been to identify and isolate compounds that show high activity against these pathogens and indeed several classes of polypeptides and proteins exhibiting antifungal activity against a variety of plant pathogenic fungi have been isolated (Bowles, 1990; Brears et al., 1994). The antifungal polypeptides and proteins include chitinases, cysteine-rich chitin-binding proteins, β-1,3-glucanases, permatins (including zeamatins), thionins, ribosome-inactivating proteins, and non-specific lipid transfer proteins, are believed to play important roles in plant defense against fungal infection. The use of natural protein products to control plant pathogens has been demonstrated, for example, in European Patent Application 0 392 225.

Recently, another group of plant proteins has been found to function as defensins in combating infections by plant pathogens (PCT International Publication WO 93/05153). Two small cysteine-rich proteins isolated from radish seed, Rs-AFP1 and RsAFP2, were found to inhibit the growth of many pathogenic fungi when the pure protein was added to an in vitro antifungal assay medium. Transgenic tobacco plants containing the gene encoding Rs-AFP2 protein were found to be more resistant to attack by fungi than non-transformed plants.

Proteins similar to radish seed RS-AFP2 have been isolated from seeds of many other plants (PCT International Publication WO 93/05153; Broekaert et al., 1995). All the proteins in this group share similarity in their amino acid sequence, but differ in their antifungal activities against various fungi, especially in the presence of different monoand divalent salts. The antifungal activity of some antifungal proteins is dramatically reduced in the presence of 1 mM $CaCl_2$ and 50 mM KCl (Terras et al., 1992). The usefulness of an antifungal protein for genetically engineering plant disease resistance can be greatly influenced by the sensitivity of the antifungal activity to salt concentration, since metal ions such as $K^+$, $Na^+$, $Ca^{2+}$, and $Mg^{2+}$ are required for normal physiological functions and are therefore abundantly present in plant cells.

Pea cDNA has been isolated following host-pathogen interactions (Chiang et al., 1991). The cDNA, pI230, is part of a group of cDNAs which accumulate in response to challenge by the pathogen Fusarium solani in both compatible Sacc. f. Sp. pisi and incompatible f. sp. phaseoli interactions. However, the protein product of this gene is unreported and its function is unknown.

Recombinant DNA technology has recently led to the development of transgenic plants which can express proteins that have antimicrobial activity against certain pests. For example, methods for transforming a wide variety of different dicotoleneous plants and obtaining transgenic plants have been reported in the literature (see Gasser and Fraley (1989); Fisk and Dandekar (1993); Christou (1994), and the references cited therein).

Similarly, methods for producing transgenic plants among the monocotyledenous plants are also well documented. Successful transformation and plant regeneration have been achieved in asparagus (Asparagus officinalis; Bytebier et al. (1987); barley (Hordeum vulgare; Wan and Lemaux (1994)); maize (Zea mays; Rhodes et al. (1988)); Gordon-Kamm et al. (1990); Fromm et al. (1990); Koziel et al. (1993); oats (Avena sativa; Somers et al. (1992)); orchardgrass (Dactylis glomerata; Horn et al. (1988)); rice (Oryza sativa, including indica and japonica varieties; Tornyama et al. (1988)); Zhang et al. (1988); Luo and Wu (1988); Zhang and Wu (1988); Christou et al. (1991); rye (Secale cereale; De la Pena et al. (1987)); sorghum (Sorghum bicolor; Cassas et al. (1993)); sugar cane (Saccharum spp.; Bower and Birch (1992)); tall fescue (Festuca arundinacea; Wang et al. (1992)); tuifgrass (Agrostis palustris; Zhong et al. (1993)); wheat (Triticum aestivum; Vasil et al. (1992); Troy Weeks et al. (1993); Becker et al. (1994)).

A number of publications have discussed the use of plant and bacterial glucanases, chitinases, and lysozymes produced in transgenic plants exhibiting increased resistance to various microorganisms such as fungi. These include EP 0 292 435, EP 0 290 123, WO 88/00976, U.S. Pat. No. 4,940,840, WO 90/07001, EP 0 392 225, EP 0 307 841, EP 0 332 104, EP 0 440 304, EP 0 418 695, EP 0 448 511, and WO 91/06312. The protection obtained from expression of osmotin-like proteins is discussed in WO 91/18984.

There is thus a continuing need to identify biocidal compounds, particularly those that will be effective against plant pathogenic fungi, whether applied as compositions directly to an infected plant or expressed in transgenic plants in amounts sufficient to provide protection against the pathogen.

2.0 SUMMARY OF THE INVENTION

2.1 Novel Antifungal Polypeptides

The present invention relates to the discovery of new antifungal polypeptides that exhibit broad spectrum antifungal activity against plant pathogenic and other fungi. The DNA encoding the polypeptides does not show significant sequence homology with other antifungal polypeptides found in plants and has been shown to express the encoded polypeptides in transformed plants in amounts sufficient to provide protection against fungus infection. The novel peptides represent a new group of protein antifungals obtainable from alfalfa plants.

In one aspect, the present invention provides an isolated antifungal polypeptide comprising the amino acid sequence shown in SEQ ID NO:2 (AlfAFP1) and SEQ ID NO: 14 (AlfAFP2), and biologically functional equivalents thereof. AlfAFP1 and AlfAFP2, or biologically functional equivalents thereof, can be isolated from plants, or produced or synthesized by any suitable method known in the art, including direct chemical synthesis, synthesis in heterologous biological systems such as microbial, plant, and animal systems, tissue cultures, cell cultures, or in vitro translation systems.

The present invention also provides isolated DNA sequences encoding the disclosed antifungal polypeptides, and genetic constructs and methods for inserting such DNA sequences into host cells for the production of the polypeptides encoded thereby. The novel nucleic acid segments comprise two alfAFP genes having the nucleotide sequence shown in FIG. 1, FIG. 2 and FIG. 3 and in SEQ ID NO:6, SEQ ID NO: 10 and SEQ ID NO:13. The coding region for AlfAFP1 is shown in FIG. 1 and for AlfAFP1 and AlfAFP2 in FIG. 3.

The present invention also provides microorganisms and plants transformed with DNA nucleotide sequences encoding the antifungal polypeptides according to the present invention.

In accomplishing the foregoing, there is provided in accordance with various aspects of the present invention:

An isolated polypeptide comprising the amino acid sequence shown in SEQ ID NO:2.

An isolated DNA molecule encoding the aforementioned polypeptide. The isolated DNA molecule may be a cDNA molecule comprising the nucleotide sequence shown in SEQ ID NO:6 or SEQ ID NO:10. Alternatively, this cDNA molecule may comprise a contiguous segment of the nucleotide sequence shown in SEQ ID NO:6 or SEQ ID NO:10 and segments hybridizable thereto under conditions of standard stringency.

A method of controlling fungal damage to a plant, comprising providing to the locus of said plant an isolated polypeptide comprising or consisting essentially of the amino acid sequence shown in SEQ ID NO:2. In this method, the polypeptide may be provided to the plant locus by plant-colonizing microorganisms which produce the antifungal polypeptide, by applying a composition comprising the isolated polypeptide thereto, or by expressing DNA encoding the polypeptide within cells of the plant.

Furthermore, the genome of this plant may comprise one or more additional DNA molecules encoding an antifungal peptide, polypeptide, or protein, wherein the additional DNA molecules are expressed and produce an antifungal effective amount of said peptide, polypeptide, or protein. The additional DNA molecule can also comprise the following:

DNA encoding a B.t. endotoxin, wherein the DNA is expressed and produces an anti-insect effective amount of B.t. endotoxin. The plant may be a member selected from the group consisting of apple, alfalfa, barley, broccoli, cabbage, canola, carrot, citrus, corn, cotton, garlic, oat, onion, an ornamental plant, pea, peanut, pepper, potato, rice, rye, sorghum, soybean, strawberry, sugarbeet, sugarcane, tomato, turf grasses, trees, vines, vegetables, and wheat. The present invention also encompasses a potato seedpiece produced by such plants.

Genes encoding AlfAFP1 and AlfAFP2, including naturally occurring muteins and variants thereof, presumably exist in the genome of various plant species. These genes can be obtained from the chromosomal DNA of plant species by conventional molecular biological methods. For example, chromosomal DNA libraries may be constructed in vectors such as the bacteriophage vectors λ EMBL3 and λgt10, cosmids, or plasmids using methods known in the art (Sambrook et al., 1989). Genes encoding polypeptides having the same as or similar antifungal activity as that of AlfAFP1 can be isolated by PCR™ performed on chromosomal DNA or chromosomal DNA libraries, or by probe hybridization of genomic DNA libraries. Primers for PCR™ and probes for hybridization screening can be designed based on the nucleotide sequence of the polypeptide cDNA shown in SEQ ID NO:10. The primers should not have self-complementary sequences nor have complementary sequences at their 3' ends in order to prevent primer-dimer formation. The primers may contain restriction sites. The primers are annealed to the DNA and sufficient cycles of PCR™ are performed to yield a product readily visualized by gel electrophoresis and staining. The primers are generally at least 16 nucleotides in length, typically at least 20 nucleotides in length, preferably at least 24 nucleotides in length, and more preferably at least 28 nucleotides in length. Such primers will be capable of specifically priming genes encoding antifungal polypeptides or proteins having the same or similar antifungal activity as AlfAFP1. The amplified fragments may be purified and inserted into an appropriate vector, and propagated by conventional means known in the art.

2.2 AlfAFP1 and AlfAFP2 DNA Segments as Hybridization Probes and Primers

In addition to their use in directing the expression of antifungal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:10 or SEQ ID NO:6 will find particular utility. Longer contiguous identical or complementary sequences, e.g., those of about 20, 30, 40, 50, 100, 200, 300, 400, 500 bp, etc. (including all intermediate lengths and up to and including the full-length sequence of 507 basepairs will also be of use in certain embodiments.

The ability of such nucleic acid probes to specifically hybridize to antifungal protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to DNA sequences of SEQ ID NO:10 or SEQ ID NO:6, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating alfalfa plant antifungal protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1993; Segal 1976; Prokop, 1991; and Kuby, 1991, are particularly relevant.

Of course, for some applications, for example, where one desires to prepare mutants employing a mutant primer strand hybridized to an underlying template or where one seeks to isolate alfalfa plant antifungal protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

The present invention provides oligonucleotide hybridization probes useful in screening genomic and other nucleic acid libraries for DNA sequences encoding peptides, polypeptides, and proteins having antifungal activity the same or similar to that of AlfAFP1 and AlfAFP2, which probes can be designed based on the sequences provided herein. In particular embodiments, such probes may range from about 16 to about 28 nucleotides in length, generally about 16 nucleotides in length, more typically about 20 nucleotides in length, preferably about 24 nucleotides in length, and more preferably about 28 nucleotides in length. Preferably, these probes specifically hybridize to genomic DNA and other DNA sequences encoding peptides, polypeptides, or proteins having the same or similar antifungal activity as that of AfAFP1 and AlfAFP2. Such oligonucleotide probes can be synthesized by automated synthesis, and may be conveniently labeled at the 5' end with a reporter molecule such as a radionuclide, e.g., $^{32}$P, or biotin.

Oligonucleotide probes such as those mentioned may be used to probe genomic or cDNA libraries. Genomic libraries for example may be constructed by fragmenting or digesting genomic DNA with a restriction enzyme such as Sau3A, ligating the DNA fragments so obtained into a suitable vector such as lambda phage and expressing in a suitable host cell, typically *E. coli*. cDNA libraries represent complementary DNA copies of mRNA and are often preferred because the clones obtained are free of the introns or other noncoding sequences found in genomic DNA. In any event, construction of genomic and cDNA libraries are well known to those skilled in the art, being described in numerous publications, e.g. Thompson and Thompson, 1991.

Once constructed, the library may be plated as colonies or phage, depending upon the vector employed, and the recombinant DNA transferred to nylon or nitrocellulose membranes. Following denaturation, neutralization, and fixation of the DNA to the membrane, the membrane is hybridized with the labeled probe (reporter molecule). Following this, the membrane is washed, and the reporter molecule detected. Colonies or phage harboring hybridizing DNA are then isolated and propagated. Candidate clones or PCR™- amplified fragments may be verified as comprising DNA encoding AlfAFP1 and AlfAFP2 or related peptides, polypeptides, or proteins having antifungal activity the same as or similar to that of AlfAFP1 and AlfAFP2 by a variety of means. For example, the candidate clones may be hybridized with a second, non-overlapping probe, or subjected to DNA sequence analysis. The antifungal activity of the peptide, polypeptide, or protein encoded thereby can be assessed by cloning and expression of the DNA in an appropriate host such as yeast or E. coli, followed by isolation of the peptide, polypeptide, or protein, and assay of the antifungal activity thereof by methods such as that described in Example 3. By such means, plant nucleic acids encoding AlfAFP1 and AlfAFP2, or peptides, polypeptides, or proteins biologically functionally equivalent thereto, useful in controlling undesired fungi and protecting plants against fungal pathogens may be isolated.

Appropriately designed degenerate oligonucleotides may be used to screen genomic libraries directly, and the isolated coding sequences may be incorporated into transformation/expression vectors. Genomic DNAs and cDNAs isolated from organisms such as higher plants may be probed using degenerate oligonucleotide sequences based on the nucleotide sequence of AlfAFP1 (SEQ ID NO:10) and AlfAFP2 (SEQ ID NO:6). The probes may be used in conjunction with PCR™ technology employing reverse transcriptase to amplify hybridizable cDNAs (E. S. Kawasaki, 1990). cDNAs are easily cloned in appropriate transformation/expression vectors and introduced into suitable host cells, e.g., plant cells of monocots and dicots. The polypeptides encoded by the DNAs can be expressed in the transformed cells and isolated using established procedures including polyacrylamide gel electrophoresis and Western blots.

Alternatively, degenerate oligonucleotides may be used as probes to screen cDNA libraries from plants in, for example, lambda phage vectors such as λ ZapII (Stratagene, La Jolla, Calif.) The cDNA isolated in this manner may be transferred to an appropriate transformation/expression vector for introduction into a host cell.

2.3 Recombinant Vectors and Antifungal Protein Expression

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a alfalfa plant antifungal protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. An appropriate promoter system contemplated for use in high-level expression includes, but is not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of alfalfa plant antifungal peptides or epitopic core regions, such as may be used to generate anti-alfalfa plant antifungal protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2 or SEQ ID NO: 14.

2.4 Alfalfa plant antifungal Protein Transgenes and Transgenic Plants

In yet another aspect, the present invention provides methods for producing a transgenic plant which expresses a nucleic acid segment encoding the novel alfalfa plant antifungal proteins of the present invention. The process of producing transgenic plants is well-known in the art. In general, the method comprises transforming a suitable host cell with a DNA segment which contains a promoter operatively linked to the alfAFP1 or alfAFP2 coding region. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant alfalfa plant antifungal protein expressed in a particular transgenic cell, the invention also provides for the expression of alfalfa plant antifungal protein antisense mRNA. The use of antisense mRNA as a means of controlling or decreasing the amount of a given protein of interest in a cell is well-known in the art.

Another aspect of the invention comprises transgenic plants which express a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more alfAFP1 or alfAFP2 transgenes, either native, synthetically modified, or mutated. In some instances, more than one transgene will be incorporated into the genome of the transformed host plant cell. Such is the case when more than one alfalfa plant antifungal protein-encoding DNA segment is incorporated into the genome of such a plant. In certain situations, it may be desirable to have one, two, three, four, or even more alfalfa plant antifungal proteins (either native or recombinantly-engineered) incorporated and stably expressed in the transformed transgenic plant.

It may also be desirable to incorporate other DNA segments into the genome of a transgenic plant where such DNA encodes other antifungal proteins non-homologous to the disclosed alfalfa antifungal proteins, or various other proteins that improve the quality of plant products or agronomic performance of the plants. Thus other types of proteins encoded by the DNA may include antibacterial, antiviral, antifungal or insecticidal proteins such as *Bacillus thuringiensis* (B.t.) proteins.

Simultaneous co-expression of multiple antifungal and/or other anti-pathogen proteins in plants is advantageous in that it exploits more than one mode of control of plant pathogens. This may, where two or more antifungal proteins are expressed, minimize the possibility of developing resistant fungal speciess, broaden the scope of resistance and potentially result in a synergistic antifungal effect, thereby enhancing the level of resistance. Co-expression with B.t. insecticidal toxin proteins is expected to provide an additional advantage in providing protection against a wide range of insect larvae. Insecticidal B.t. toxin proteins have been expressed in several varieties of plants, including cereal plants.

Other proteins conferring certain advantages may likewise be coexpressed with the DNAs encoding the polypeptides of the present invention; including: (1) DNAs encoding enzymes such as glucose oxidase (which converts glucose to gluconic acid, concomitantly producing hydrogen peroxide which confers broad spectrum resistance to plant pathogens); pyruvate oxidase; oxylate oxidase; cholesterol oxidase; amino acid oxidases; and other oxidases that use molecular oxygen as a primary or secondary substrates to produce peroxides, including hydrogen peroxide; (2) pathogenesis related proteins such as SAR8.2a and SARB.2b proteins; the acidic and basic forms of tobacco PR-1a, PR-1b, PR-1c, PR-1', PR-2, PR-3, PR-4, PR-5, PR-N, PR-O, PR-O', PR-P, PR-Q, PR-S, and PR-R proteins; chitinases such as tobacco basic chitinase and cucumber chitinase/lysozyme; peroxidases such as cucumber basic peroxidase; glucanases such as tobacco basic glucanase; osmotin-like proteins; (3) viral capsid proteins and replicases of plant viruses; (4) plant R-genes (resistance genes), such as Arabidopsis RPS2 (Bent et al., 1994), Arabidopsis RPM1 (Grant et al., 1995), tobacco N-gene and N'-gene (Whitham et al., 1994), tomato Cf-9 (Jones et al., 1994), flax L6 (Ellis et al., 1995), and rice Xa21 (Song et al., 1995). These genes can be expressed using constitutive promoters, tissue-specific promoters, or promoters inducible by fungal pathogens or other biological or chemical inducers; (5) pathogen Avr genes, such as *Cladosporium fulvum* Avr9 (Van Den Ackerveken et al., 1992), that can be expressed using pathogen- or chemical-inducible promoters; and (6) genes that are involved in the biosynthesis of salicylic acid, such as benzoic acid 2-hydroxylase (Leon et al., 1995).

For purposes of protection against pathogenic fungi, a preferred gene which may be introduced includes, for example, an alfalfa plant antifungal protein-encoding DNA sequence from plant origin, and particularly one or more of those described herein which are obtained from Medicago or any of those sequences which have been genetically engineered to decrease or increase the antifungal activity of alfalfa plant antifungal proteins in such a transformed host cell. However, it is believed that highly homologous antifungal proteins with similar antifungal activity will also be found in other plant species, including but not limited to the following:

Arabidopsis, barley, broccoli, cabbage, canola, carrot, corn, garlic, onion, pea, pepper, potato, rice, soybean, sugarbeet, tobacco, tomato, and wheat;

microorganisms such as Aspergillus, Penicilium, Streptomvces, Alternaria (*Alternaria brassicola; Alternaria solani*); Ascochyta (*Ascochyta pisi*); Botrytis (*Botrytis cinerea*); Cercospora (*Cercospora kikuchii; Cercospora zaea-maydis*); Colletotrichum (*Colletotrichum lindemuthianum*), Diplodia (*Diplodia maydis*); Erysiphe (*Erysiphe graminis* f.sp. *graminis; Erysiphe graminis* f.sp. *hordei*); Fusariunu (*Fusarium nivale; Fusarium oxysporum; Fusarium graminearum; Fusarium culmorum; Fusarium solani; Fusarium moniliforme; Fusarium roseum*); Gaeumanomyces (*Gaeumnanomyces graminis* f.sp. *tritici*); Helminthosporium (*Helminthosporium turcicum; Helminthosporium carbonum; Helminthosporium maydis*); Macrophomina (*Macrophomina phaseolina; Maganaporthe grisea*); Nectria (*Nectria heamatococca*), Peronospora (*Peronospora manshurica; Peronospora tabacina*), Phoma (*Phoma betae*); Phymatotrichum (*Phymatotrichum omnivorum*), Phytophthora (*Phytophthora icinnamomi; Phytophthora cactorum; Phytophthora phaseoli; Phytophthora parasitica; Phytophthora citrophthora, Phytophthora megasperma* f.sp. *sojae; Phytophthora infestans*), Plasmopara (*Plasmopara viticola*); Podosphaera (*Podosphaera leucotricha*), Puccinia (*Puccinia sorghi; Puccinia striiformis; Puccinia graminis* f.sp. *tritici; Puccinia asparagi; Puccinia recondita; Puccinia arachidis*), Pythium (*Pythium aphanidermatum*); Pyrenophora (*Pyrenophora tritici-repentens*); Pyricularia (*Pyricularia oryzae*); Pythium (*Pythium ultitnum*); Rhizoctonia (*Rhizoctonia solani; Rhizoctonia cerealis*); Scerotium (*Scerotium rolfisii*); Sclerotinia (*Sclerotinia sclerotiorum*); Septoria (*Septoria lycopersici; Septoria glycines; Septoria nodorum; Septoria tritici*); Thielaviopsis (*Thielaviopsis basicola*); Uncinula (*Uncinula necator*); Venturia (*Venturia inaequalis*); and Verticillium (*Verticillium dahliae; Verticillium albo-atrum*); and other nonplant organisms.

Preferred nucleic acid sequences are those obtained from alfalfa plant seeds or any of those sequences which have been genetically engineered to decrease or increase the antifungal activity of alfalfa plant antifungal proteins in such a transformed host cell.

Means for transforming a plant cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed alfalfa plant antifungal proteins. These DNA constructs can further include structures such as promoters, enhancers, polylinkers, or even gene sequences which have positively- or negatively-regulating activity upon the particular genes of interest as desired. The DNA segment or gene may encode either a native or modified alfalfa plant antifungal protein, which will be expressed in the resultant recombinant cells, and/or which will impart an improved phenotype to the regenerated plant.

Such transgenic plants may be desirable for increasing the antifungal resistance of a monocotyledonous or dicotyledonous plant, by incorporating into such a plant, a transgenic DNA segment encoding one or more AlfAFP1 or AlfAFP2 alfalfa plant antifungal proteins which is toxic to fungi. Particularly preferred plants include wheat, vegetables, ornamental plants, fruit trees, apple, alfalfa, barley, broccoli, cabbage, canola, carrot, citrus, corn, cotton, garlic, oat, onion, ornamental plants, pea, peanut, pepper, potato, rice, rye, sorghum, soybean, strawberry, sugarbeet, sugarcane, tomato, turf grasses, trees, vines and the like.

In a related aspect, the present invention also encompasses a seed produced by the transformed plant, a progeny from such seed, and a seed produced by the progeny of the original transgenic plant, produced in accordance with the above process. Such progeny and seeds will have an alfalfa plant antifungal protein-encoding transgene stably incorporated into their genome, and such progeny plants will inherit the traits afforded by the introduction of a stable transgene in Mendelian fashion. All such transgenic plants having incorporated into their genome transgenic DNA segments encoding one or more AlfAFP1 or AlfAFP2 alfalfa plant antifungal proteins or polypeptides are aspects of this invention.

2.4.1 Expression in Monocots

Alfalfa, from which AlfAFP1 and AlfAFP2 were isolated, is a dicot. As discussed by Campbell et al. (1990), while a clear difference in codon usage patterns exists between monocots and dicots, it is known that monocots express genes resembling those found in dicots. Based on this observation, it appears that codon usage in dicot genes would not present a great barrier to expression of dicot genes in monocots. In any event, those of ordinary skill in the art are familiar with the principles governing the adaptation of codon usage to suit the host plant (see Murray et al., 1989), and the expression of DNA constructs is now routine in the art.

2.5 Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

2.6 AlfAFP1 and AlfAFP2 Antibody Compositions and Methods of Making Antibodies In particular embodiments, the inventors contemplate the use of antibodies, either monoclonal or polyclonal which bind to the alfalfa plant antifungal proteins disclosed herein. Means for preparing and characterizing antibodies are well known in the art (See, e.g., Antibodies: A Laboratory Manual, Cold Spring Harbor Laboratory, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include using glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified antifungal protein, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, 1986, pp. 65–66; Campbell, 1984, pp. 75–83). For example, where the immunized animal is a mouse, one may use P3-X63/Ag8, X63-Ag8.653, NS 1/1.Ag 4 1, Sp210-Ag14, FO, NSO/U, MPC-11, MPC11-X45-GTG 1.7 and S194/5XX0 Bu1; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71–74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.7 ELISAs and Immunoprecipitation

ELISAs may be used in conjunction with the invention. In an ELISA assay, proteins or peptides incorporating alfalfa plant antifungal protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with an alkaline phosphatase or peroxidase-conjugated anti-rabbit IgG for a period of time and under conditions which favor the development of immunocomplex formation (e.g., incubation for 2 hours at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-alfalfa plant antifungal protein antibodies of the present invention are particularly useful for the isolation of other alfalfa plant antifungal protein antigens by immunoprecipitation. Immunoprecipitation involves the separation of the target antigen component from a complex mixture, and is used to discriminate or isolate minute amounts of protein. For the isolation of membrane proteins, cells must be solubilized into detergent micelles. Nonionic salts are preferred, since other agents, such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

2.8 Western Blots

The compositions of the present invention will find great use in immunoblot or Western blot analysis. The anti-peptide antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Particularly useful immunologically-based detection labels for use in conjunction with Western blotting include enzymatically-, radiolabel-, or fluorescently-tagged secondary antibodies against the antifungal moiety.

2.9 Alfalfa Plant Antifungal Protein Screening and Detection Kits

The present invention contemplates methods and kits for screening samples suspected of containing alfalfa plant antifungal protein polypeptides or alfalfa plant antifungal protein-related polypeptides, or cells producing such polypeptides. A kit may contain one or more antibodies of the present invention, and may also contain reagent(s) for detecting an interaction between a sample and an antibody of the present invention. The provided reagent(s) can be radio-, fluorescently- or enzymatically-labeled. The kit can contain a known radiolabeled agent capable of binding or interacting with a nucleic acid or antibody of the present invention.

The reagent(s) of the kit may be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chromatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the alfalfa plant antifungal proteins or peptides of the present invention may be employed to detect antibodies having reactivity therewith, or, alternatively, antibodies prepared in accordance with the present invention, may be employed to detect alfalfa plant antifungal proteins or alfalfa plant antifungal protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either an alfalfa plant antifungal protein or peptide or an alfalfa plant antifungal protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of alfalfa plant antifungal proteins or related peptides and/or antibodies in a sample. Samples may include cells, cell supernatants, cell suspensions, cell extracts, enzyme fractions, protein extracts, or other cell-free compositions suspected of containing alfalfa plant antifungal proteins or peptides. Generally speaking, kits in accordance with the present invention will include a suitable alfalfa plant antifungal protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.10 Compositions Epitopic Core Sequences

The present invention is also directed to protein or peptide compositions, free from total cells and other peptides, which comprise a purified protein or peptide which incorporates an epitope that is immunologically cross-reactive with one or more anti-alfalfa plant antifungal protein antibodies. In particular, the invention concerns epitopic core sequences derived from alfalfa plant antifungal proteins or peptides.

As used herein, the term "incorporating an epitope(s) that is immunologically cross-reactive with one or more anti-alfalfa plant antifungal protein antibodies" is intended to refer to a peptide or protein antigen which includes a primary, secondary or tertiary structure similar to an epitope located within a alfalfa plant antifungal protein or polypeptide. The level of similarity will generally be to such a degree that monoclonal or polyclonal antibodies directed against the alfalfa plant antifungal protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of alfalfa plant antifungal protein immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic alfalfa plant antifungal protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to alfalfa plant antifungal proteins, and in particular to AlfAFP-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the alfalfa plant antifungal protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

2.11 Biological Functional Equivalents

2.11.1 Peptides, Polypeptides, and Proteins Containing Conservative Amino Acid Changes in the Fundamental Polypeptide Sequence Peptides, polypeptides, and proteins biologically functionally equivalent to AlfAFP1 and AlfAFP2 include amino acid sequences containing conservative amino acid changes in the fundamental sequences shown in SEQ ID NO:2 or SEQ ID NO:14. In such amino acid sequences, one or more amino acids in the fundamental sequence is (are) substituted with another amino acid(s), the charge and polarity of which is similar to that of the native amino acid, i.e., a conservative amino acid substitution, resulting in a silent change.

Substitutes for an amino acid within the fundamental polypeptide sequence can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cyteine, cystine, tyrosine, asparagine, and glutamine; (4) neutral nonpolar (hydrophobic) amino acids such as alanine, leucine, isoleucine, valine, proline, phenylalanine, tryptophan, and methionine.

Conservative amino acid changes within the fundamental polypeptide sequence can be made by substituting one amino acid within one of these groups with another amino acid within the same group. Biologically functional equivalents of AlfAFP1 and AlfAFP2 can have 10 or fewer conservative amino acid changes, more preferably seven or fewer conservative amino acid changes, and most preferably five or fewer conservative amino acid changes. The encoding nucleotide sequence (gene, plasmid DNA, cDNA, or synthetic DNA) will thus have corresponding base substitutions, permitting it to encode biologically functional equivalent forms of AlfAFP1 and AlfAFP2.

The biologically functional equivalent peptides, polypeptides, and proteins contemplated herein should possess about 80% or greater sequence similarity, preferably about 85% or greater sequence similarity, and most preferably about 90% or greater sequence similarity, to the sequence of, or corresponding moiety within, the fundamental AlfAFP1 and AlfAFP2 amino acid sequence.

As indicated, modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated alfalfa plant antifungal proteins are contemplated to be useful for increasing the antifungal activity of the protein, and consequently increasing the antifungal activity and/or expression of the recombinant transgene in a plant cell. The amino acid changes may be achieved by changing the codons of the DNA sequence, according to the codons given in Table 2.

TABLE 2

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

2.11.2 Fragments and Variants of AlfAFP

While the antifungal polypeptide of the present invention preferably comprises the amino acid sequence shown in SEQ ID NO:2 and SEQ ID NO:14, fragments and variants of this sequence possessing the same or similar antifungal activity as that of this antifungal polypeptide are also encompassed by the present invention. Thus contiguous sequences of 8 or more amino acids in SEQ ID NO:2 or SEQ ID NO:14 may exhibit such activity, including for example SEQ ID NO:1.

Fragments of AlfAFP1 and AlfAFP2 can be truncated forms wherein one or more amino acids are deleted from the N-terminal end, C-terminal end, the middle of the polypeptide, or combinations thereof. These fragments can be naturally occurring or synthetic mutants of AlfAFP1 and AlfAFP2, and should retain the antifungal activity of AlfAFP1 and AlfAFP2.

Variants of AlfAFP1 and AlfAFP2 include forms wherein one or more amino acids has(have) been inserted into the natural sequence. These variants can also be naturally occurring or synthetic mutants of AlfAFP1 and AlfAFP2, and should retain the antifungal activity of AlfAFP1 and AlfAFP2.

Combinations of the foregoing, i.e., forms of the antifungal polypeptide containing both amino acid deletions and additions, are also encompassed by the present invention. Amino acid substitutions can also be present therein as well.

The fragments and variants of AlfAFP1 and AlfAFP2 encompassed by the present invention should preferably possess about 70%–75% or greater sequence similarity, more preferably about 80%, 85%, 88% or greater sequence similarity, and most preferably about 90% or 95% or greater sequence similarity, to the corresponding regions of AlfAFP1 and AlfAFP2 having the corresponding amino acid sequences shown in SEQ ID NO:2 and SEQ ID NO:14.

2.11.3 Other Biologically Functional Equivalent Forms of AlfAFP

Other biologically functional equivalent forms of AlfAFP1 and AlfAFP2 useful in the present invention include conjugates of the polypeptides, or biologically functional equivalents thereof as described above, with other peptides, polypeptides, or proteins, forming fusion products therewith exhibiting the same, similar, or greater antifungal activity as compared with that of AlfAFP1 and AlfAFP2 having the amino acid sequence shown in SEQ ID NO:2 or SEQ ID NO:14.

2.12 Protein Compositions

An antifungal composition, comprising an antifungal effective amount of one or more of the isolated antifungal polypeptides of the present invention are contemplated. Preferred compositions comprise the amino acid sequence shown in SEQ ID NO:2 and SEQ ID NO:14, and an acceptable carrier. The antifungal composition may be used for inhibiting the growth of, or killing, pathogenic fungi. The compositions can be formulated by conventional methods such as those described in, for example, WinnackerKuchler (1986); van Falkenberg (1972–1973); and K. Martens (1979). Necessary formulation aids, such as carriers, inert materials, surfactants, solvents, and other additives are also well known in the art, and are described, for example, in Watkins (YEAR), and Winnacker-Kuchler (1986). Using these formulations, it is also possible to prepare mixtures of the present antifungal polypeptide with other antifungally active substances, fertilizers and/or growth regulators, etc., in the form of finished formulations or tank mixes.

Antifungal compositions contemplated herein also include those in the form of host cells, such as bacterial and fungal cells, capable of the producing the present antifungal polypeptide, and which can colonize roots and/or leaves of plants. Examples of bacterial cells that can be used in this manner include strains of Agrobacterium, Arthrobacter, Azospyrillum, Clavibacter, Escherichia, Pseudomonas, Rhizobacterium, Yeast and the like.

Numerous conventional fungal antibiotics and chemical fungicides with which the present antifungal polypeptide can be combined are known in the art and are described in Worthington and Walker (1983). These include, for example, polyoxines, nikkomycines, carboxyamides, aromatic carbohydrates, carboxines, morpholines, inhibitors of sterol biosynthesis, and organophosphorus compounds. Other active ingredients which can be formulated in combination with the present antifungal polypeptide include, for example, insecticides, attractants, sterilizing agents, acaricides, nematocides, and herbicides. U.S. Pat. No. 5,421, 839 contains a comprehensive summary of the many active agents with which substances such as the present antifungal polypeptide can be formulated.

Whether alone or in combination with other active agents, the antifungal polypeptides of the present invention should be applied at a concentration in the range of from about 0.1 mg/ml to about 100 mg/ml, preferably between about 5 mg/ml and about 50 mg/ml, at a pH in the range of from about 3 to about 9. Such compositions may be buffered using, for example, phosphate buffers between about 1 mM and 1 M, preferably between about 10 mM and 100 mM, more preferably between about 15 mM and 50 mM.

AlfAFP1, AlfAFP2 and biologically functional equivalents are therefore expected to be useful in controlling fungi in a wide variety of plants, exemplified by those in the following genera and species:

Alternaria (*Alternaria brassicola; Alternaria solani*);
Ascochyta (*Ascochyta pisi*);
Botrytis (*Botrytis cinerea*);
Cercospora (*Cercospora kikuchii; Cercospora zaeamaydis*);
Colletotrichum (*Colletotrichum lindemuthianum*);
Diplodia (*Diplodia maydis*);
Erysiphe (*Erysiphe graminis* f.sp. *graminis; Erysiphe graminis* f.sp. *hordei*);
Fusarium (*Fusarium nivale; Fusarium oxysporum; Fusarium graminearum; Fusarium culmorum; Fusarium solani; Fusarium moniliformne; Fusarium roseum*);
Gaeumanomyces (*Gaeumanomyces graminis* f.sp. *tritici*);
Helminthosporium (*Helminthosporium turcicum; Helminthosporium carbonum; Helminthosporium maydis*);
Macrophomina (*Macrophomina phaseolina; Maganaporthe grisea*);
Nectria (*Nectria heamatococca*);
Peronospora (*Peronospora manshurica; Peronospora tabacina*);
Phoma (*Phoma betae*);
Phymatotrichum (*Phymatotrichum omnivorum*);
Phytophthora (*Phytophthora cinnamomi; Phytophthora cactorum; Phytophthora phaseoli; Phytophthora parasitica; Phytophthora citrophthora;*
Phytophthora megaspermaf.sp. *sojae; Phytophthora infestans*);
Plasmopara (*Plasmopara viticola*);
Podosphaera (*Podosphaera leucotricha*);
Puccinia (*Puccinia sorghi; Puccinia striiformis; Puccinia graminis* f.sp. *tritici; Puccinia asparagi; Puccinia recondita; Puccinia arachidis*);
Pythium (*Pythium aphanidermatum*);
Pyrenophora (*Pyrenophora tritici-repentens*);
Pyricularia (*Pyricularia oryzae*);
Pythium (*Pythium ultimum*);
Rhizoctonia (*Rhizoctonia solani; Rhizoctonia cerealis*);
Scerotium (*Scerotium rolfsii*);
Sclerotinia (*Sclerotinia sclerotiorum*);
Septoria (*Septoria Iycopersici; Septoria glycines; Septoria nodorunim; Septoria tritici*);
Thielaviopsis (*Thielaviopsis basicola*);
Uncinula (*Uncinula necator*);
Venturia (*Venturia inaequalis*);
Verticillium (*Verticillium dahliae; Verticillium alboatrum*)

Further scope of the applicability of the present invention will become apparent from the detailed description and drawings provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

3.0 DESCRIPTION OF THE DRAWINGS

The above and other objects, features, and advantages of the present invention will be better understood from the following detailed description taken in conjunction with the accompanying drawings, all of which are given by way of illustration only and are not limitative of the present invention.

DNA fragments common to the plasmid maps presented herein are: AMP: ampicillin resistance; ori-pUC: replication origin derived from pUC plasmid; LAC: partial sequence of the Lac Z gene; p-e35S: promoter e35S; HSP70 intron: the intron of heat shock protein 70 from maize; NOS3': 3' untranslated region of the nopaline synthase (nos) gene of Agrobacterium Ti plasmid; ori-M13: M13 phage replication origin; Spc/Str: bacterial spectinomycin/streptomycin resistance gene; p-FMV: figwort mosaic virus 35S promoter; EPSPS/CTP2: chloroplast transit peptide from the Arabidopsis 5-enopyruvyl-3-phosphoshikimate synthase gene (EPSPS); CP4 syn: synthetic bacterial glyphosate resistance CP4 5-enolpyruvyl-3-phosphoshikimate synthase (EPSPS) gene; E9 3': 3' untranslated region of the pea ssRUBISCO E9 gene; PetHSP70-Leader: 5' untranslated leader sequence of petunia heat shock protein 70 gene; ori-322: pUC322 replication origin.

FIG. 1 shows the cDNA nucleotide sequence and deduced amino acid sequence of AlfAFP1. The triangle indicates the start of the mature AlfAFP1 polypeptide. The underlined amino acid sequence indicates the signal peptide. The double underlined sequence indicates a potential polyA signal sequence. The asterisk denotes the stop codon.

FIG. 2 is a pileup comparison of AlfAFP1, AlfAFP2, and pI230. All amino acid sequences except AlfAFP1 are derived from cDNA sequences and include both a signal peptide and a mature protein. The lines indicate conserved amino acid residues. The mature protein of AlfAFP1 is indicated in bold.

FIG. 3 is an alignment of the recovered 5' cDNAs of AlfAFP1 and AlfAFP2.

Common bases are indicated with astreses.

Figure 5:
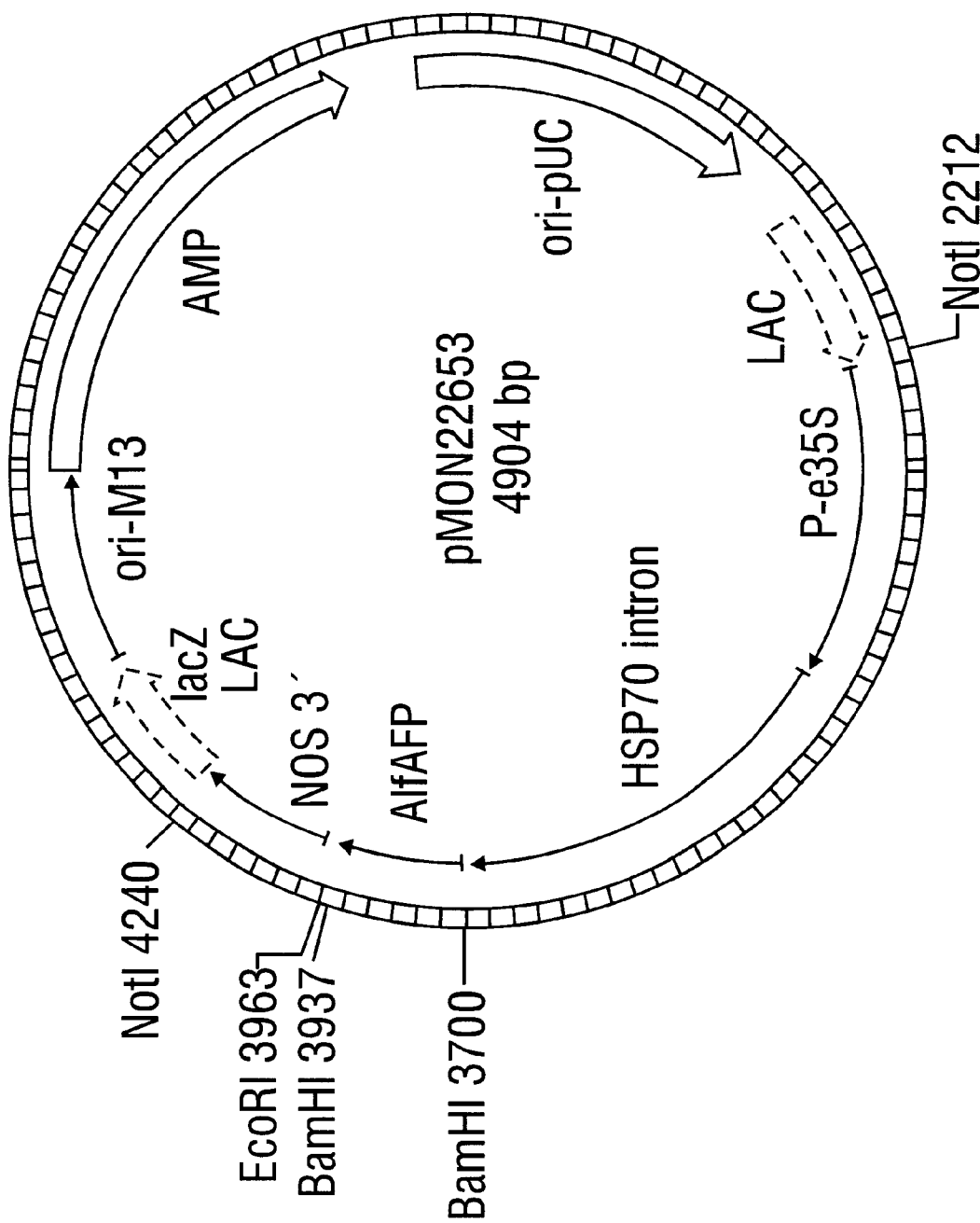
Figure 6:
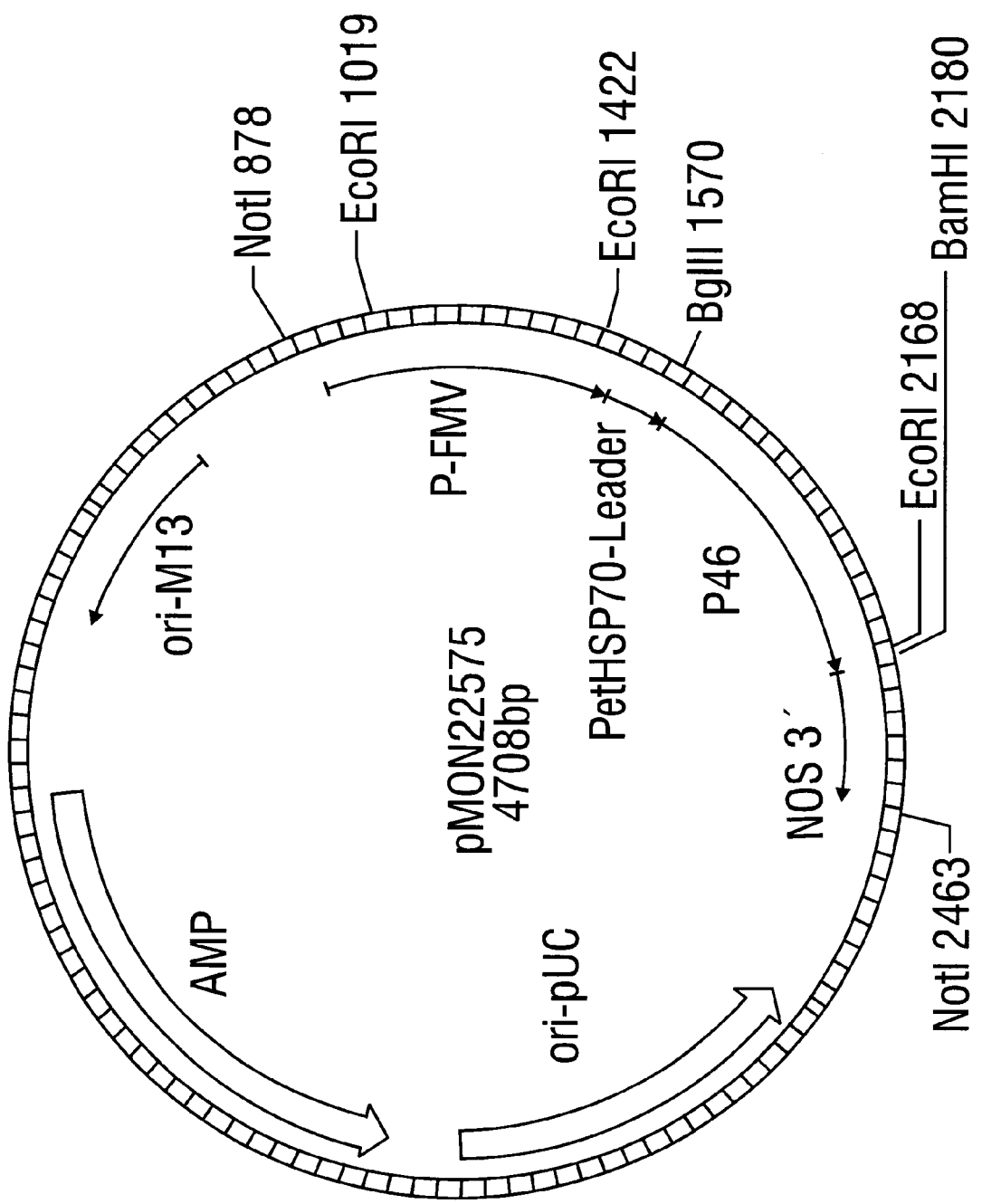
Figure 7:
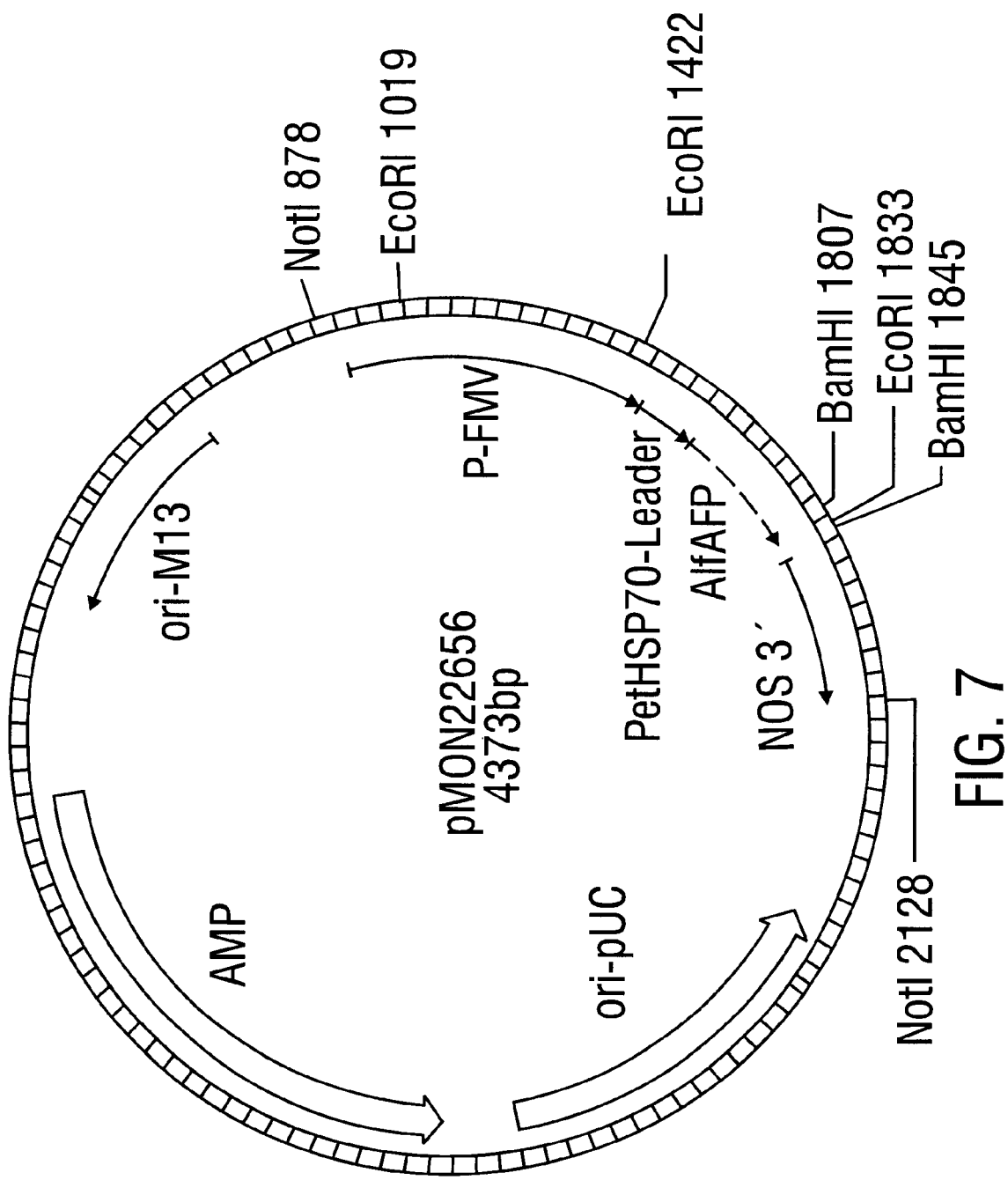
Figure 8:
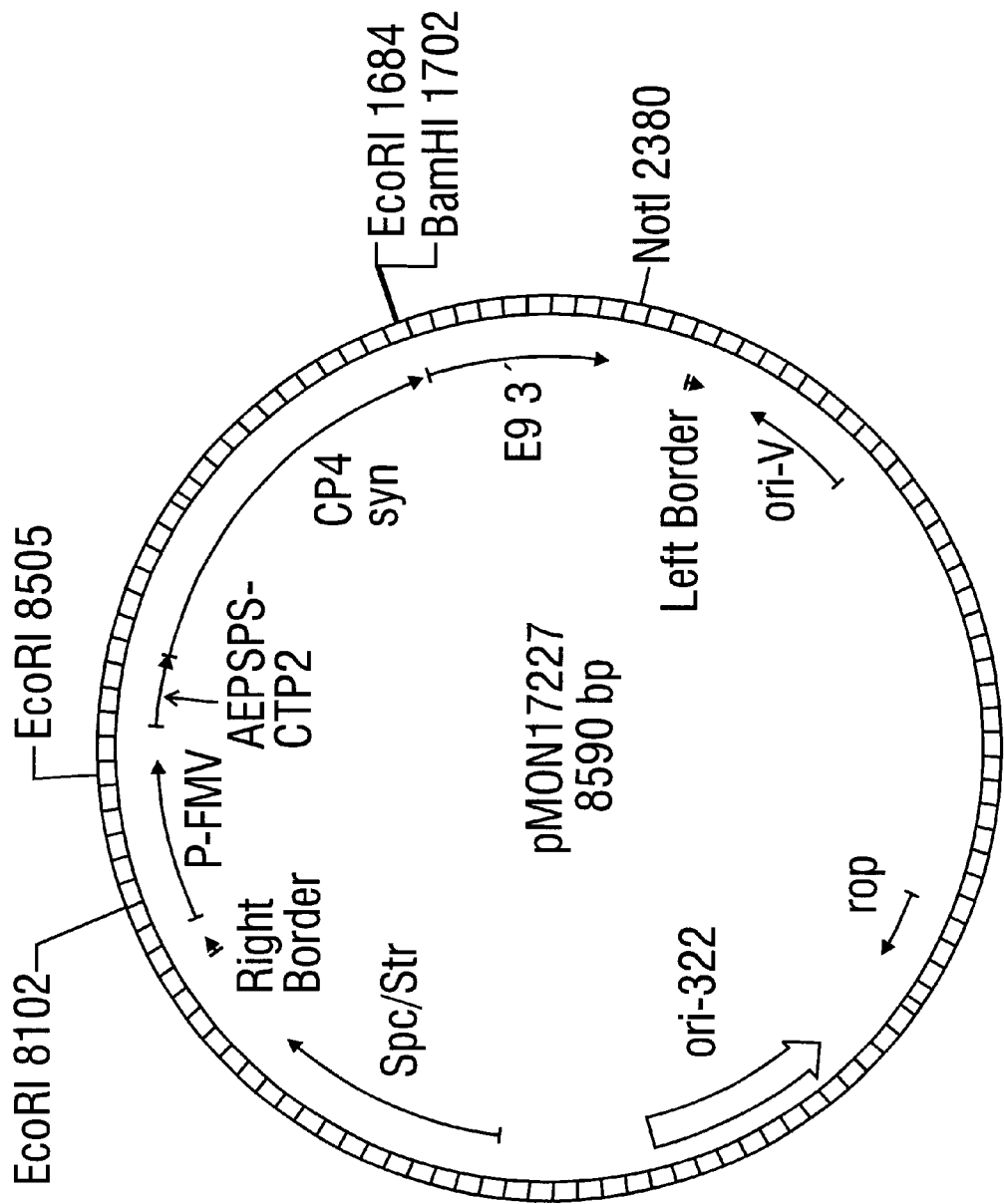
Figure 9:
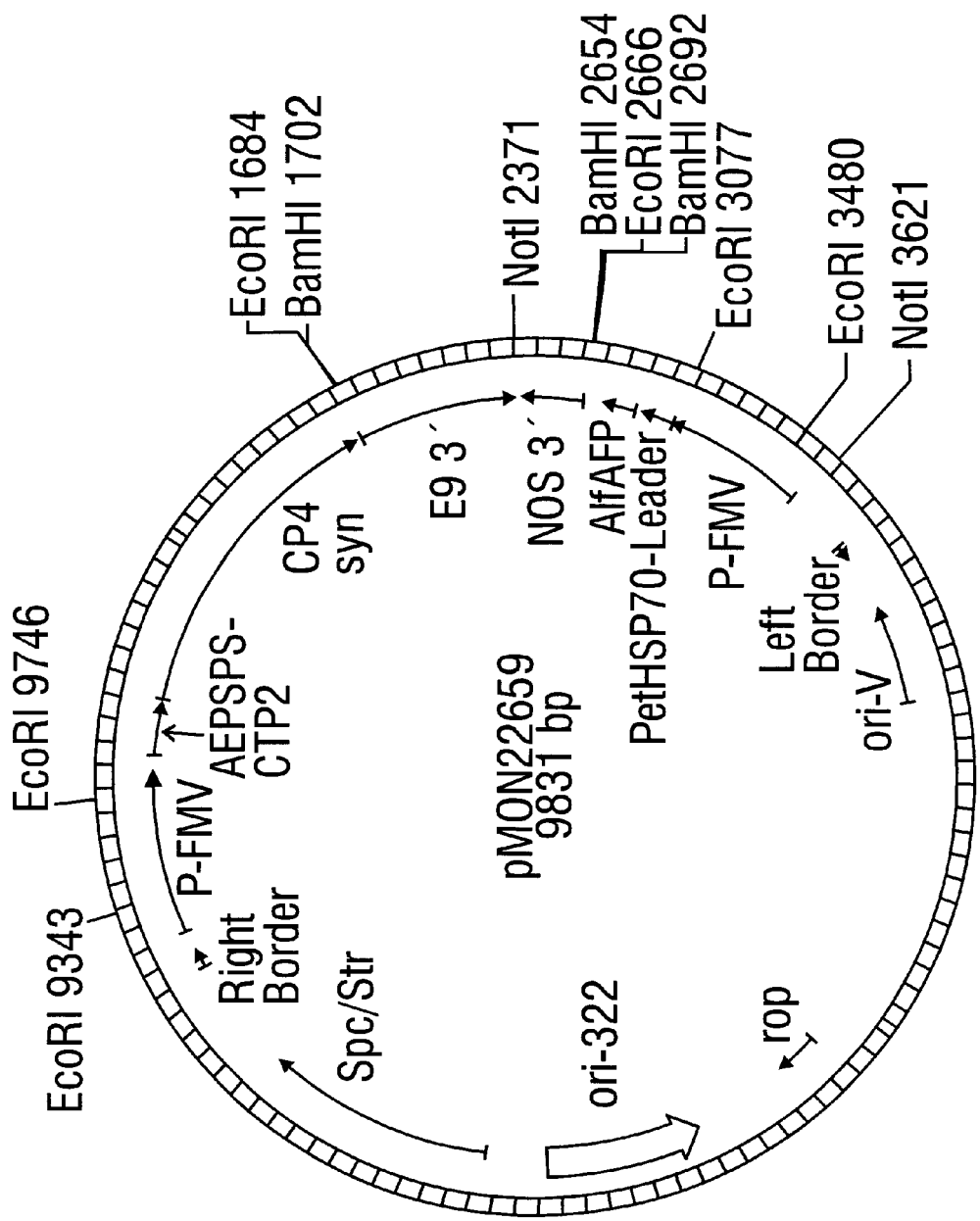
Figure 10:
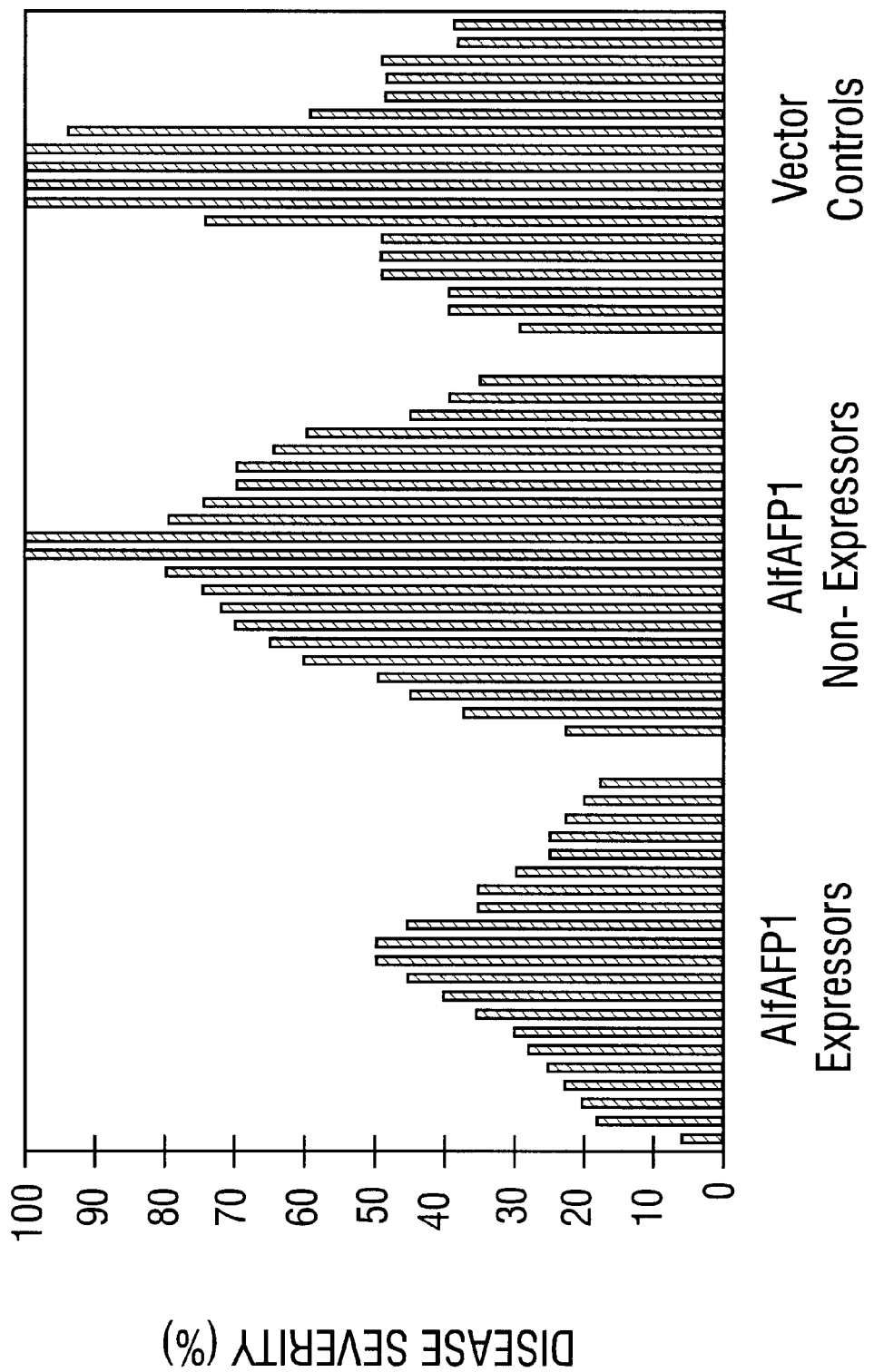

FIG. 4 is a physical map of pMON23317.
FIG. 5 is a physical map of pMON22653.
FIG. 6 is a physical map of pMON22575.
FIG. 7 is a physical map of pMON22656.
FIG. 8 is a physical map of pMON17227.
FIG. 9 is a physical map of pMON22659.
FIG. 10 is a bar graph, corresponding to the data in Table 2, showing the results of a Verticillium wilt disease test conducted on transgenic potato plants expressing AlfAFP1 cDNA.

4.0 DESCRIPTION OF ILLUSTRATIVE EMBODIMENTS

4.1

The work described herein has identified cDNAs and other nucleic acids which are capable of conferring resistance to fungal pathogens when incorporated as transgenes in susceptible plants. Agronomic, horticultural, ornamental, and other economically or commercially useful plants can be made resistant to fungal pathogens by introducing these DNAs in a functionally operable manner so that they are expressed at a level effective to confer resistance to fungal pathogens upon these plants.

4.2 Definitions

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or plant. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same species. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

Biological functional equivalents. As used herein such equivalents with respect to the antifungal proteins of the present invention are peptides, polypeptides and proteins that contain a sequence or moiety exhibiting sequence similarity to the novel peptides of the present invention, such as AlfAFP1 and AlfAFP2, and which exhibit the same or similar functional properties as that of the polypeptides disclosed herein, including antifungal activity. Biological equivalents also include peptides, polypeptides and proteins that react with, i.e. specifically bind to antibodies raised against AlfAFP1 and AlfAFP2 and that exhibit the same or similar antifungal activity, including both monoclonal and polyclonal antibodies.

Antifungal polypeptide refers to a polypeptide having antifungal properties, e.g., which inhibits the growth of fungal cells, or which kills fungal cells, or which disrupts or retards stages of the fungal life cycle such as spore germination, sporulation, or mating.

Combating or Controlling Fungal Damage in an agricultural context refers to reduction in damage to a crop due to infection by a fungal pathogen. More generally, this phrase refers to reduction in the adverse effects caused by the presence of an undesired fungus in any particular locus.

Structural Coding Sequence refers to a DNA sequence that encodes a peptide, polypeptide, or protein that is made by a cell following transcription of the structural coding sequence to messenger RNA (mRNA), followed by translation of the mRNA to the desired peptide, polypeptide, or protein product.

4.3 Probes and Primers

DNA sequence information provided by the invention allows for the preparation of relatively short DNA (or RNA) sequences having the ability to specifically hybridize to gene sequences of the selected polynucleotides disclosed herein. Nucleic acid probes of an appropriate length may be prepared based on a consideration of a selected alfalfa plant antifungal protein gene sequence, e.g., a sequence such as that shown in SEQ ID NO:10 or SEQ ID NO:13. The ability of such DNAs and nucleic acid probes to specifically hybridize to a alfalfa plant antifungal protein gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a alfalfa plant antifungal protein gene from Medicago using PCR™ technology. Segments of related alfalfa plant antifungal protein genes from other species may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a alfalfa plant antifungal protein-encoding sequence, such as that shown in SEQ ID NO:10 or SEQ ID NO:13. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

4.4 Recombinant Vectors

The present invention contemplates an expression vector comprising a polynucleotide of the present invention. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

In an alternate embodiment, the recombinant expression of DNAs encoding the alfalfa plant antifungal proteins of the present invention is performed using a transformed Gram-negative bacterium such as an E. coli or Pseudomonas spp. host cell. Promoters which function in high-level expression of target polypeptides in E. coli and other Gram-negative host cells are also well-known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

4.4.1 Promoters

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

As discussed, the expression of DNA encoding AlfAFP1 and AlfAFP2 in plant cells can be placed under the control of the naturally occurring homologous promoter, or a variety of heterologous promoters. A number of promoters active in plant cells have been described in the literature. These include, for example, the nopaline synthase (nos), mannopine synthase (mas), and octopine synthase (ocs) promoters, which are carried on tumor-inducing plasmids of Agrobacterium tumefaciens; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel et al., 1995); the chitinase promoter from Arabidopsis (Samac et al., 1991); the LTP (Lipid Transfer Protein) promoters from broccoli (Pyee et al., 1995); the ubiquitin promoter from maize (Christensen et al., 1992); and the actin promoter from rice (McElroy et al., 1990). All of these promoters have been used to create various types of DNA constructs that have been expressed in plants. See, for example, PCT International Publication WO 84/02913 in this regard.

Promoters useful in DNA constructs applicable to the methods of the present invention may be selected based upon their ability to confer specific expression of a coding sequence in response to fungal infection. The infection of plants by fungal pathogens triggers the induction of a wide array of proteins, termed defense-related or pathogenesis-related (PR) proteins (Bowles, 1990; Bol et al., 1990; Linthorst, 1991). Such defense-related or PR genes may encode enzymes involved in phenylpropanoid metabolism (e.g., phenylalanine ammonia lyase, chalcone synthase), proteins that modify plant cell walls (e.g., hydroxyproline-rich glycoproteins, glycine-rich proteins, peroxidases), enzymes that degrade fungal cell walls (e.g., chitinases, glucanases), thaumatin-like proteins, or proteins of as yet unknown function. Defense-related or PR genes have been isolated and characterized from a number of plant species. The promoters of these genes may be used to drive expression of AlfAFP1 and AlfAFP2 and biologically functional equivalents thereof in transgenic plants challenged with fungal pathogens. For example, such promoters have been derived from defense-related or PR genes isolated from potato plants (Fritzemeier et al., 1987; Cuypers et al., 1988; Logemann et al., 1989; Matton et al., 1989; Schroder et al., 1992). Alternatively, pathogen-inducible promoters such as the PRP 1 promoter obtainable from tobacco (Martini et al., 1993) may be employed.

Promoters may also be selected based upon their ability to confer specific expression in tissues where AlfAFP1 and AlfAFP2 protein is most effective, such as in the flowering parts of the plant (Weigel, 1995).

In any event, the particular promoter selected to drive the expression of AlfAFP1 and AlfAFP2 in transgenic plants should be capable of promoting expression of an antifungally effective amount of AlfAFP1 and AlfAFP2 in plant tissues. Examples of constitutive promoters capable of driving such expression are the e35S , FMV 35S , rice actin, maize ubiquitin, and eIF-4A promoters.

Promoters used in the DNA constructs of the present invention may be modified, if desired, to affect their control characteristics. For example, the CaMV 35S promoter can be ligated to the portion of the ssRUBISCO gene that represses the expression of ssRUBISCO in the absence of light, thereby creating a promoter active in leaves but not in roots. For purposes of the present invention, the phrase "CaMV35S " promoter includes variations of the CaMV35S promoter, e.g., promoters derived by means of ligation with operator regions, random or controlled mutagenesis, etc. Furthermore, promoters useful in the present invention may be altered to contain multiple enhancer sequences to assist in elevating the level of gene expression. Examples of such enhancer sequences have been reported by Kay et al. (1987).

Where the promoter is a near-constitutive promoter such as CaMV35S , increases in polypeptide expression are found in a variety of transformed plant tissues (e.g., callus, leaf, seed, and root). Alternatively, the effects of transformation can be directed to specific plant tissues by using plant integrating vectors containing a tissue-specific promoter.

An exemplary tissue-specific promoter is the lectin promoter, which is specific for seed tissue. The Lectin protein in soybean seeds is encoded by a single gene (Le 1) that is only expressed during seed maturation and accounts for about 2 to about 5% of total seed mRNA. The lectin gene and seed-specific promoter have been fully characterized and used to direct seed specific expression in transgenic tobacco plants (Vodkin et al., 1983; Lindstrom et al., 1990.)

4.4.2 Expression Vectors

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer antifungal activity to a cell is preferably an AlfAFP1 or AlfAFP2 gene. In preferred embodiments, such a polypeptide has the amino acid residue sequence of SEQ ID NO:2 or SEQ ID NO:14, or a functional equivalent of those sequences. In accordance with such embodiments, a coding region comprising the DNA sequence of SEQ ID NO:10 or the DNA sequence of SEQ ID NO:13 is also preferred.

A transgenic plant of the present invention produced from a plant cell transformed with a tissue specific promoter may be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al, 1985), pea small subunit RuBP carboxylase (Poulsen et al., 1986; Cashmore et al., 1983), Ti plasmid mannopine synthase (Langridge et al, 1989), Ti plasmid nopaline synthase (Langridge et al., 1989), petunia chalcone isomerase (Van Tunen et al., 1988), bean glycine rich protein 1 (Keller et al., 1989), CaMV35s transcript (Odell et al., 1985) and Potato patatin (Wenzler et al., 1989). Preferred promoters are the cauliflower mosaic virus (CaMV35S ) promoter and the S-E9 small subunit RuBP carboxylase promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* (Rogers et al., 1987). However, several other plant integrating vector systems are known to function in plants including pCaMVCN transfer control vector (Fromm et al., 1985). Plasmid pCaMVCN (available from Pharmacia, Piscataway, N.J.) includes the cauliflower mosaic virus CaMV35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region (Rogers et al., 1988).

3' non-translated regions of the chimeric constructs of the present invention should contain a transcriptional terminator, or an element having equivalent function, and a polyadenylation signal that functions in plants to cause the addition of adenylate nucleotides to the 3' end of the mRNA. Examples of such 3' regions include the 3' transcribed, nontranslated regions containing the polyadenylation signal of Agrobacterium tumor-inducing (Ti) plasmid genes, such as the nopaline synthase (nos) gene, and plant genes such as the soybean 7s storage protein gene and pea ssRUBISCO E9 gene (Fischoff et al., European Patent Application 0 385 962). These elements may be combined, as an example, to provide a recombinant, double-stranded DNA molecule, comprising operatively linked in the 5' to 3' direction:

a) a promoter that functions in a plant cell to cause the production of an RNA sequence;

b) a DNA coding sequence that encodes AlfAFP1 or AlfAFP2; and c) a 3' non-translated region that functions in the plant cell to cause transcriptional termination and the addition of polyadenylate nucleotides to the 3' end of said RNA sequence.

AlfAFP1 and AlfAFP2 DNA coding sequences may comprise the entire nucleotide sequence shown in SEQ ID NO:13 or SEQ ID NO:6 or any portion thereof that may have functional equivalence, such as truncated versions. Alternatively, it may be desirable to express epitopic regions of the antifungal polypeptides in order to use these peptides to raise antibodies against the antifungal polypeptides.

Typically, DNA sequences located a few hundred base pairs downstream of the polyadenylation site serve to terminate transcription. The DNA sequences are referred to herein as transcription-termination regions. The regions are required for efficient polyadenylation of transcribed messenger RNA (mRNA) and are known as 3' nontranslated regions. RNA polymerase transcribes a coding DNA sequence through a site where polyadenylation occurs.

Translational enhancers may also be incorporated as part of the vector DNA. Thus the DNA constructs of the present invention should also preferably contain one or more 5' non-translated leader sequences which may serve to enhance expression of the gene products from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence (Griffiths, et al, 1993).

Such "enhancer" sequences may be desirable to increase or alter the translational efficiency of the resultant mRNA. The present invention is not limited to constructs where the enhancer is derived from the native 5' non-translated promoter sequence, but may also include non-translated leader sequences derived from other non-related promoters such as other enhancer transcriptional activators or genes. For example, the petunia heat shock protein 70 (Hsp70) contains such a leader (Winter, 1988).

4.4.3 DNA Constructs for Expression of AlfAFP in Transgenic Plants

As noted above, the present invention provides DNA constructs or expression vectors that facilitate the expression of the DNA sequences discussed herein in higher plants and various microorganisms. As used herein, the terms "vector construct" or "expression vector" refer to assemblies of DNA fragments operatively linked in a functional manner that direct the expression of the DNA sequences discussed herein, as well as any additional sequence(s) or gene(s) of interest.

The expression of a plant structural coding sequence (gene, cDNA, synthetic DNA, or other DNA) which exists in double-stranded DNA form involves transcription of messenger RNA (mRNA) from one strand of the DNA by RNA polymerase enzyme and subsequent processing of the mRNA primary transcript inside the nucleus. This processing involves a 3' non-translated region which adds polyadenylate nucleotides to the 3' end of the mRNA.

Transcription of DNA into mRNA is regulated by a region of DNA referred to as the "promoter." The promoter region contains a sequence of bases that signals RNA polymerase to associate with the DNA and initiate transcription of mRNA using one of the DNA strands as a template to make a corresponding strand of RNA.

Vectors useful in the present invention therefore include promoter elements operably linked to coding sequences of interest, and can also include 5' non-translated leader sequences, 3' non-translated regions, and one or more selectable markers. A variety of such markers are well known in the art.

4.4.4 Nucleotide Sequences Biologically Functionally Equivalent to the cDNA Sequence The present invention includes not only the cDNA sequence shown in SEQ ID NO:13 or SEQ ID NO:6 but also biologically functionally equivalent nucleotide sequences. The phrase "biologically functionally equivalent nucleotide sequences" denotes DNAs and RNAs, including genomic DNA, plasmid DNA, cDNA, synthetic DNA, and mRNA nucleotide sequences, that encode peptides, polypeptides, and proteins exhibiting the same or similar antifungal activity as that of AlfAFP1 and AlfAFP2, i.e., when introduced into host cells in a functionally operable manner so that they are expressed, they produce peptides, polypeptides, or proteins exhibiting antifungal activity at a level sufficient to confer resistance to fungal pathogens upon host cells or plants.

4.4.5 Nucleotide Sequences Encoding Conservative Amino Acid Changes in AlfAFP Biologically functional equivalent nucleotide sequences of the present invention include nucleotide sequences encoding conservative amino acid changes within the fundamental AlfAFP1 and AlfAFP2 amino acid sequence, producing silent changes therein. Such nucleotide sequences contain corresponding base substitutions compared to nucleotide sequences encoding wild-type AlfAFP1 and AlfAFP2.

4.4.6 Nucleotide Sequences Containing Base Substitutions, Additions, or Deletions In addition to nucleotide sequences encoding conservative amino acid changes within the fundamental AlfAFP1 and AlfAFP2 polypeptide sequence, biologically functional equivalent nucleotide sequences of the present invention include nucleotide sequences containing other base substitutions, additions, or deletions. These include nucleic acids containing the same inherent genetic information as that contained in the cDNA of SEQ ID NO:13 or SEQ ID NO:6 and which encode peptides, polypeptides, or proteins conferring fungal resistance the same as or similar to that of AlfAFP1 and AlfAFP2 upon host cells and plants. Such nucleotide sequences can be referred to as "genetically equivalent modified forms" of the cDNA shown in SEQ ID NO:13 or SEQ ID NO:6, and can be identified by the methods described herein.

Mutations made in the cDNA, plasmid DNA, genomic DNA, synthetic DNA, or other nucleic acid encoding AlfAFP1 and AlfAFP2 preferably preserve the reading frame of the coding sequence. Furthermore, these mutations preferably do not create complementary regions that could hybridize to produce secondary mRNA structures, such as loops or hairpins, that would adversely affect mRNA translation.

Although mutation sites can be predetermined, it is not necessary that the nature of the mutations per se be predetermined. For example, in order to select for optimum characteristics of mutants at a given site, random mutagenesis can be conducted at the target codon.

Alternatively, mutations can be introduced at particular loci by synthesizing oligonucleotides containing a mutant sequence, flanked by restriction sites enabling ligation to fragments of the native AlfAFP1 or AlfAFP2 cDNA sequences. Following ligation, the resulting reconstructed nucleotide sequence encodes a derivative form of AlfAFP1 or AlfAFP2 having the desired amino acid insertion, substitution, or deletion.

In either case, the expressed mutants can be screened for desired antifungal activity by, for example, the method described in Example 3.

Specific examples of useful genetically equivalent modified forms of the cDNA of SEQ ID NO:13 or SEQ ID NO:6 include DNAs having a nucleotide sequence which exhibits a high level of homology, i.e., sequence identity, to the cDNA of SEQ ID NO:13 or SEQ ID NO:6. This can range from about 70% or greater sequence identity, more preferably from about 80% or greater sequence identity, and most preferably from about 90% or greater sequence identity, to the cDNA or corresponding moiety thereof of SEQ ID NO:13 or SEQ ID NO:6.

Such genetically equivalent modified forms can be readily isolated using conventional DNA-DNA or DNA-RNA hybridization techniques (Sambrook et al., 1989) or by amplification using Polymerase Chain Reaction (PCR™) methods. These forms should possess the ability to confer resistance to fungal pathogens when introduced by conventional transformation techniques into plant cells normally sensitive to such pathogens.

4.4.7 Nucleotide Sequences Encoding Fragments and Variants of AlfAFP

The fragments and variants of AlfAFP1 and AlfAFP2 discussed in Example 5 may be encoded by cDNA, plasmid DNA, genomic DNA, synthetic DNA, or mRNA. These nucleic acids should possess about 70% or greater sequence similarity, preferably about 80% or greater sequence similarity, and most preferably about 90% or greater sequence similarity, to corresponding regions or moieties of the cDNA having the nucleotide sequence shown in SEQ ID NO:13 and SEQ ID NO:6 encoding AlfAFP1 and AlfAFP2, or the mRNA corresponding thereto.

In the present invention, nucleic acids biologically functional equivalent to the cDNAs of AlfAFP1 and AlfAFP2 having the nucleotide sequence shown in SEQ ID NO:13 and SEQ ID NO:6 include:

(1) DNAs having a length which has been altered either by natural or artificial mutations such as partial nucleotide deletion, insertion, addition, or the like, so that when the entire length of SEQ ID NO:13 is taken as 100%, the biologically functional equivalent sequence has an approximate length of 60–120% of that of SEQ ID NO:13 or SEQ ID NO:6, preferably 80–110% thereof; or (2) nucleotide sequences containing partial (usually 20% or less, preferably 10% or less, more preferably 5% or less of the entire length) natural or artificial mutations so that such sequences code for different amino acids, but wherein the resulting polypeptide retains the antifungal activity of AlfAFP1 and AlfAFP2. The mutated DNAs created in this manner usually encode a polypeptide having 70% or greater, preferably 80% or greater, and more preferably 90% or greater, sequence identity to the amino acid sequence of AlfAFP1 and AlfAFP2 (SEQ ID NO:2) encoded by the nucleotide sequence of SEQ ID NO:13 and SEQ ID NO:6.

In the present invention, the methods employed to create artificial mutations are not specifically limited, and such mutations can be produced by any of the means conventional in the art.

For example, the cDNA or gene of AlfAFP1 or AlfAFP2 may be treated with appropriate restriction enzymes so as to insert or delete appropriate DNA fragments so that the proper amino acid reading frame is preserved. Subsequent to restriction endonuclease treatment, the digested DNA can be treated to fill in any overhangs, and the DNA religated.

Mutations can also be introduced at particular loci by synthesizing oligonucleotides containing a mutant sequence flanked by restriction sites enabling ligation to fragments of the native AlfAFP1 or AlfAFP2 cDNA or genomic sequence. Following ligation, the resulting reconstructed sequence encodes a derivative having the desired amino acid insertion, substitution, or deletion.

Alternatively, oligonucleotide-directed site-specific or segment-specific mutagenesis procedures can be employed to produce an altered cDNA or genomic DNA sequence having particular codons altered according to the substitution, deletion, or insertion desired.

Exemplary methods of making the alterations described above are disclosed by Ausubel et al. (1995); Bauer et al. (1985); Craik (1985); Frits Eckstein et al. (1982); Sambrook et al. (1989); Smith et al. (1981); Osuna et al. (1994); and Walder et al (1986). Biologically functional equivalents to the cDNA sequence disclosed herein produced by any of these methods can be selected for by assaying the peptide, polypeptide, or protein encoded thereby using the techniques described in Example 3.

4.4.8 Nucleotide Sequences Encoding Peptides, Polypeptides, and Proteins That React With Antibodies Raised Against AlfAFP Biologically functional equivalent forms of the cDNA encoding AlfAFP1 and AlfAFP2 include nucleotide sequences that encode peptides, polypeptides, and proteins that react with, i.e., specifically bind to, antibodies raised against AlfAFP1 and AlfAFP2, and that exhibit the same or similar antifungal activity as this polypeptide. Such antibodies can be polyclonal or monoclonal antibodies.

4.4.9 Genetically Degenerate Nucleotide Sequences

Due to the degeneracy of the genetic code, i.e., the existence of more than one codon for most of the amino acids naturally occurring in proteins, other DNA (and RNA) sequences that contain essentially the same genetic information as the cDNA of the present invention, and which encode substantially the same amino acid sequence as that encoded by the nucleotide sequence of SEQ ID NO:13 or SEQ ID NO:6, can be used in practicing the present invention. This principle applies as well to any of the other nucleotide sequences discussed herein.

4.4.10 Synthetic DNA Sequences Designed for Enhanced Expression in Particular Host Cells Biologically functional equivalent forms of the cDNA of the present invention also include synthetic DNAs designed for enhanced expression in particular host cells. Host cells often display a preferred pattern of codon usage (Murray et al., 1989). Synthetic DNAs designed to enhance expression in a particular host should therefore reflect the pattern of codon usage in the host cell.

In the present invention, sequence similarity or identity can be determined using the "BestFit" or "Gap" programs of the Sequence Analysis Software Package, Genetics Computer Group, Inc., University of Wisconsin Biotechnology Center, Madison, Wis. 53711.

4.4.11 Nucleotide Sequences Encoding Fused Forms of AlfAFP

Other biologically functional equivalent forms of the cDNA of SEQ ID NO:13 or SEQ ID NO:6 useful in the present invention include those which have been modified to encode conjugates with other peptides, polypeptides, or proteins such as those discussed under "Summary of the Invention" and in Example 5, thereby encoding fusion products therewith.

4.4.12 Biologically Functional Equivalent Forms of AlfAFP cDNA Detected by Hybridization Although one embodiment of a nucleotide sequence encoding AlfAFP1 and AlfAFP2 is shown in SEQ ID NO:13 or SEQ ID NO:6, it should be understood that the present invention also includes nucleotide sequences that hybridize to the sequence of SEQ ID NO:13 and SEQ ID NO:6 and their complementary sequences, and that encode peptides, polypeptides, or proteins having the same or similar antifungal activity as that of AlfAFP1 and AlfAFP2. Such nucleotide sequences preferably hybridize to SEQ ID NO:13 and SEQ ID NO:6 or their complementary sequences under conditions of moderate to high stringency (see Sambrook et al., 1989). Exemplary conditions include initial hybridization in 6×SSC, 5×Denhardt's solution, 100 mg/ml fish sperm DNA, 0.1% SDS, at 55° C. for sufficient time to permit hybridization (e.g., several hours to overnight), followed by washing two times for 15 min each in 2×SSC, 0.1% SDS, at room temperature, and two times for 15 min each in 0.5–1× SSC, 0.1% SDS, at 55° C., followed by autoradiography. Typically, the nucleic acid molecule is capable of hybridizing when the hybridization mixture is washed at least one time in 0.1×SSC at 55° C., preferably at 60° C., and more preferably at 65° C.

The present invention also encompasses nucleotide sequences that hybridize to the cDNA of SEQ ID NO:13 and SEQ ID NO:6 under salt and temperature conditions equivalent to those described above, and that encode a peptide, polypeptide, or protein that has the same or similar antifungal activity as that of AlfAFP1 and AlfAFP2 disclosed herein.

The nucleotide sequences described above are considered to possess a biological function substantially equivalent to that of the cDNA of SEQ ID NO:13 and SEQ ID NO:6 encoding AlfAFP1 and AlfAFP2 if they encode peptides, polypeptides, or proteins having an antifungal effect differing from that of AlfAFP1 and AlfAFP2 by about 25% or less.

4.4.13 Peptides, Polypeptides, and Proteins That React With Antibodies Raised Against AlfAFP Biologically functional equivalent forms of AfAFP1 and AlfAFP2 also include peptides, polypeptides, and proteins that react with, i.e., specifically bind to, antibodies raised against AlfAFP1 and AlfAFP2, and that exhibit the same or similar antifungal activity as this polypeptide. Such antibodies can be polyclonal or monoclonal antibodies.

4.5 Characteristics of the Novel Antifungal Proteins

The present invention provides novel polypeptides that define a whole or a portion of an AlfAFP1 or AlfAFP2 antifungal protein. AlfAFP1 is a polypeptide having a molecular weight of about 5,186 daltons. SDS gel electrophoresis showed an approximate molecular weight of 6 kDa. Amino acid sequence was determined as described in Example 2 and bioefficacy in Example 3. Amino acid sequence includes 45 amino acids shown in SEQ ID NO:2.

4.7 Transformed Host Cells and Transgenic Plants

Methods and compositions for transforming a bacterium, a yeast cell, a plant cell, or an entire plant with one or more expression vectors comprising an alfalfa plant antifungal protein-encoding gene segment are further aspects of this disclosure. A transgenic bacterium, yeast cell, plant cell or plant derived from such a transformation process or the progeny and seeds from such a transgenic plant are also further embodiments of the invention.

Means for transforming bacteria and yeast cells are well known in the art. Typically, means of transformation are similar to those well known means used to transform other bacteria or yeast such as *E. coli* or *Saccharomyces cerevisiae*. Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant species may not necessarily be the most effective for another plant species, but it is well known which methods are useful for a particular plant species.

There are many methods for introducing transforming DNA segments into cells, but not all are suitable for delivering DNA to plant cells. Suitable methods are believed to include virtually any method by which DNA can be introduced into a cell, such as by Agrobacterium infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well-known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

4.7.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect A transformation by electroporation one may employ either friable tissues such as a suspension culture of cells, or embryogenic callus, or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.7.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducing stably transforming monocots, is that neither the isolation of protoplasts (Cristou et al., 1988) nor the susceptibility to Agrobacterium infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

4.7.3 Agrobacterium-Mediated Transfer

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described (Fraley et al., 1985; Rogers et al., 1987). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern Agrobacterium transformation vectors are capable of replication in *E. coli* as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate construction of vectors capable of expressing various polypeptide coding genes. The vectors described (Rogers et al., 1987), have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant species where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Although monocots appear not to be natural hosts for Agrobacterium, transformation has been achieved in asparagus using Agrobacterium vectors as described (Bytebier et al., 1987).

A transgenic plant formed using Agrobacterium transformation methods typically contains a single gene on one chromosome. Such transgenic plants can be referred to as being heterozygous for the added gene. However, insomuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced, and analyzing the resulting plants produced for enhanced transgene activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

4.7.4 Other Transformation Methods

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant species depends upon the ability to regenerate that particular plant species from protoplasts. Illustrative methods for the regeneration of cereals from protoplasts are described (Fujimura et al., 1985; Toriyama et al., 1986; Yamada et al., 1986; Abdullah et al., 1986).

To transform plant specieS that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized. (Vasil, 1992)

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

4.8 Methods for Producing Fungus-Resistant Transgenic Plants

By transforming a suitable host cell, such as a plant cell, with a recombinant alfAFP1 and/or alfAFP2 gene-containing segment, the expression of the encoded alfalfa plant antifungal protein can result in the formation of fungus-resistant plants.

By way of example, one may utilize an expression vector containing a coding region for an alfalfa plant antifungal protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the antifungal proteins.

The formation of transgenic plants may also be accomplished using other methods of cell transformation which are known in the art such as Agrobacterium-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described (Horsch et al., 1985). In this procedure, transformants are cultured in the presence of a selection agent and in a medium that induces the regeneration of shoots in the plant species being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant species employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., an alfAFP gene) that encodes the AlfAFP polypeptide of interest. A preferred transgenic plant is an independent segregant and can transmit that gene and its activity to its progeny; for example a transgenic plant homozygous for that gene or a gene in a heterozygous stage, and transmits that gene to all of its offspring on sexual mating. Vegetative propagation or grafting may also be used to obtain clones. Additionally, seed from a transgenic plant may be grown in the field or greenhouse, and resulting sexually mature transgenic plants are self-pollinated to generate true breeding plants. The progeny from these plants become true breeding lines that are evaluated for, by way of example, increased antifungal capacity against fungal pathogens, preferably in the field, under a range of environmental conditions. The inventors contemplate that the present invention will find particular utility in the creation of transgenic plants of commercial interest including various turf grasses, wheat, corn, rice, barley, oats, potato, soybean, cotton, berries such as strawberries, a variety of ornamental plants and vegetables, as well as a number of nut- and fruit-bearing trees and plants.

4.9 Production of Transgenic Potato Plants Expressing AlfAFP1 and Results of Disease Tests for Verticillium Wilt Control Transgenic plants that express antifungal effective amounts of AlfAFP1 and AlfAFP2 and biologically functional equivalents thereof can be produced by:

(a) transforming plant cells with a recombinant DNA molecule comprising operatively linked in sequence in the 5' to 3' direction:

(i) a promoter region that directs the transcription of a gene in plants;

(ii) a DNA coding sequence that encodes an RNA sequence which encodes AlfAFP1 and AlfAFP2 or a biologically functionally equivalent thereof having the same or similar antifungal activity as that of AlfAFP1 or AlfAFP2; and (iii) a 3' non-translated region that encodes a polyadenylation signal which functions in plant cells to cause transcriptional termination and the addition of polyadenylate nucleotides to the 3' end of said RNA sequence;

(b) selecting plant cells that have been transformed;

(c) regenerating plant cells that have been transformed to produce differentiated plants; and (d) selecting a transformed plant, cells of which express said DNA coding sequence and produce an antifungal effective amount of AlfAFP1 or AlfAFP2 or said biologically functionally equivalent thereof.

The method of the present invention can be carried out in a variety of ways. The antifungal polypeptides, prepared by any of the methods noted above, may be applied directly to plants in a mixture with carriers or other additives, including other antifungal agents, as is known in the art. Alternatively, the polypeptides may be expressed by bacterial or yeast cells that can be applied to the plant, some of which may be symbiotic with the plants. Plant cells may also be transformed by conventional means to contain DNA encoding the antifungal polypeptides. These may be expressed constitutively, in a tissue-specific manner, or upon exposure of the plant to a fungal pathogen.

The amino acid sequences of the new alfalfa plant antifungal polypeptides have been determined by direct sequencing and by translation of the cloned cDNA. The homologies differ from other plant defensin type antifungal polypeptides. The most closely related polypeptide sequence is from a pea mRNA (pI230) which has a 70% homology. A pile-up diagram comparing the amino acid sequence of AlfAFP1 with that of pI230 is shown in FIG. 2.

The present invention also encompasses the use of any of the DNA sequences or biologically functional equivalents thereof disclosed herein to produce recombinant plasmids, transformed microorganisms, probes, and primers useful in identifying related DNA sequences that confer resistance to fungal pathogens on plant cells, and to produce transgenic plants resistant to such fungal pathogens.

As noted above, the antifungal polypeptides of the present invention may be used in combination with chemicals as well as other antifungal agents, including other peptides, polypeptides, and proteins that exhibit antifungal activity, so as to provide a broader spectrum of activity, i.e., to control additional pathogens, and/or to provide multiple modes of action for the control of the same fungal pathogen. Examples of such other antifungal agents include chitinases, cysteine-rich chitin-binding proteins, B-1,3-glucanases, permatins (including zeamatins), thionins, ribosome-inactivating proteins, and non-specific lipid transfer proteins.

The following detailed description of the invention is provided to aid those skilled in the art in practicing the present invention. Even so, the following detailed description should not be construed to unduly limit the present invention as modifications and variations in the embodiments discussed herein may be made by those of ordinary skill in the art without departing from the spirit or scope of the present inventive discovery.

5.0 EXAMPLES

The present invention can be better understood from the following illustrative, non-limiting Examples.

5.1 EXAMPLE 1

The molecular weight of AlfAFP1 was initially determined electrophoretically by the method of Laemmli (1970). The polypeptide was dissolved in denaturing sample buffer containing 450 mM Tris-HCl, pH 8.45, 12% glycerol, 4% SDS, 0.06% Coomassie Blue G, and 0.0025% Phenol Red (Novex, San Diego, Calif., boiled for 10 min., and electrophoresed in a 16% Tricine gel (Novex, San Diego, Calif.) in electrophoresis buffer containing 100 mM Tris, 100 mM Tricine, and 1% SDS at 125V constant voltage for two hours. Silver staining (Integrated Separation Systems, Natick, Mass.) revealed a band having a molecular weight of approximately 6 kDa.

AlfAFP1 was mass-analyzed by positive ion electrospray mass spectrometry as described by Scoble et al., (1993). The observed molecular weight of the native polypeptide was approximately 5,186 daltons.

5.2 EXAMPLE 2
Amino Acid Sequence of AlfAFP1

In order to determine the amino acid sequence of AlfAFP1, purified polypeptide (greater than 98% pure based on the mass spectrometric data) was denatured in 8 M urea containing 8 mM dithiothreitol. Cysteine residues were modified by S-carboxy-methylation as described by Stone et al., (1993). Reagents were removed by dialysis against distilled water using a membrane having a molecular weight cut-off of 1,000 kDa. Automated Edman degradation was carried out on an Applied Biosystems model 470A Protein Sequenator (Applied Biosystems, Norwalk, Conn.). The respective PTH-amino acid derivatives were identified by reversed phase analysis in an on-line fashion employing an Applied Biosystems Model 120 PTH Analyzer.

N-terminal sequencing of the polypeptide identified 43 amino acids as shown in SEQ ID NO:1 with ambiguous calls at positions 40 and 41. Information derived from mass spectrometric analysis of the polypeptide indicated that the polypeptide contained 45 amino acids and that the undetermined amino acid residues were tryptophan at position 40, cysteine at position 41, arginine at position 44 and cysteine at position 45.

The complete amino acid sequence of the mature AlfAFP1 poly-peptide is shown in SEQ ID NO:2. The polypeptide has a calculated molecular weight of 5,187 that matches the determined molecular weight of 5,186 (Example 1).

5.3 EXAMPLE 3
Bioefficacy of AlfAFP1

The antifungal activity of AlfAFP1 (SEQ ID NO:2) is expressed as the concentration in pg/ml required to cause 50% inhibition of fungal hyphal growth ($IC_{50}$). Percent fungal hyphal growth inhibition is defined as 100×the ratio of the average hyphae length in the test sample culture divided by the average hyphae length in the control culture in which buffer is added in place of the polypeptide sample.

The antifungal activity of AlfAFP1 was determined by measuring the inhibition of fungal hyphal length of a number of different fungi in the presence of this polypeptide under an inverted microscope. Fungal spores ($2 \times 10^4$ spores/ml) were allowed to germinate for 5 to 15 hours, depending on the fungus used in the test, in 50 $\mu$l of double strength testing medium. The final single strength assay medium contained: $K_2HPO_4$ (2.5 mM), $MgSO_4$ (50 $\mu$M), $CaCl_2$ (50 $\mu$M), $FeSO_4$ (5 $\mu$M), $CoCl_2$ (0.1 $\mu$M), $CuSO_4$ (0.1 $\mu$M), $Na_2MoO_4$ (2 $\mu$pM), $H_3BO_3$ (0.5 $\mu$M), KI (0.1 $\mu$M), $ZnSO_4$ (0.5 $\mu$M), $MnSO_4$ (0.1 $\mu$M), glucose (10 g/l), asparagine (1 g/l), methionine (20 mg/l), myo-inositol (2 mg/l), biotin (0.2 mg/l), thiamine-HCl (1 mg/l), and pyridoxine-HCl (0.2 mg/l). For studies on the antagonistic effect of cations, $CaCl_2$ and KCl were added to final concentrations of 1 mM and 50 mM, respectively. This salt-supplemented medium is referred to as "high salt medium," and the original medium is referred to as "low salt medium." After spore germination, 50 $\mu$l of a filter-sterilized solution of polypeptide in distilled water were added to the testing well containing the germinated spores, and the mixture was incubated for 15 to 24 hours at 24° C. AlfAFP1 was tested in a concentration range from 0 to 80 $\mu$g/ml to determine $IC_{50}$ values. Polypeptide concentrations were determined using the BCA protein assay kit obtained from Pierce (Rockford, Ill.).

Table 1 shows the antifungal activity of AlfAFP1 against Fusarium culmorum, the causal agent of wheat head scab, and Verticillium dahliae, the causal agent of early die in potato.

TABLE 1

Antifungal Activity of AlfAFP1

| | $IC_{50}$ ($\mu$g/ml) | |
| --- | --- | --- |
| Fungus | Low salt | High salt |
| F. culmorum | 1 | 15 |
| V. dahliae | 4 | 15 |

The data in Table 1 demonstrate that AlfAFP1 exhibits potent antifungal activity against Fusarium and Verticillium, which cause disease on many crop plants, including barley, corn, cotton, oat, potato, soybean, tomato, and wheat. The antifungal activity of this polypeptide is much less sensitive to the antagonistic effect of salt present in the assay medium compared to that of other antifungal peptides disclosed in PCT International Publication No. WO 93/05153. The concentration in $\mu$g/ml required to cause 50% inhibition of fungal hyphal growth ($IC_{50}$) can be realistically achieved in plants transformed with DNA encoding AlfAFP1 or AlfAFP2. These IC$_{50}$ values fall in the range of that of many commercially available fungicides, and reflect the utility of employing this antifungal polypeptide at the infection site on plants.

5.4.1 EXAMPLE 4

Cloning of AlfAFP cDNAs mRNA Isolation

Total RNA was prepared from Alfalfa seed, using the RNaide Plus Kit from Bio 101 Inc. (La Jolla, Calif.) following the protocol suggested by the manufacturer. mRNA or polyadenylated RNA was isolated using oligo(dT) cellulose (GIBCO BRL/Life Technologies, Gaithersburg, Md.) as described by Celano et al., (1993).

5.4.2 cDNA Cloning

The 5' region of the polypeptide cDNA was cloned using the 5' RACE Kit (GIBCO BRUL/Life Technologies, Gaithersburg, Md.). First strand cDNA was generated from polyadenylated RNA by reverse transcription using an oligo-dT primer. After removal of the mRNA strand by RNase H1 digestion and spin cartridge separation, a poly-C tail was added to the single stranded cDNA using a terminal deoxynucleotide transferase under conditions recommended by the enzyme manufacturer. The 5' region of the polypeptide gene was amplified by PCR™ using the GeneAmp DNA Amplification Reagent Kit (Perkin Elmer Cetus) and the reaction conditions recommended by the manufacturer.

The two primers used for amplification were: 1) mixed oligonucleotide 33-mers (14 nucleotides for cloning sites and 19 nucleotides for gene specificity, degeneracy of 32, SEQ ID NO:3 ) made to amino acids 35 to 41 at the C-terminus of the polypeptide sequence in the antisense orientation ; and 2) an oligo-dG primer that aneals to the poly-C tail of the cDNA (SEQ ID NO:4). PCR™ reaction products were analyzed by agarose gel electrophoresis, and a single band of about 330 bp was present in the complete reaction mixture but not in the control reaction mixture that contained only one primer. This band was cut out of the gel and the DNA was isolated using an Ultrafree-MC centrifugation filter unit (Millipore, Bedford, Mass.). The DNA fragment was digested with BamHI, cloned into the plasmid pGEM11Zf(+) (Promega, Madison, Wis.), and the insert sequenced on an 373 DNA Sequencer Stretch Model from Applied Biosystem using the PRISM Ready Reaction Dideoxy Terminator Cycle Sequencing Kit (Applied Biosystems).

Two different homologs of the AlfAFP cDNA were isolated. One clone, AlfAFP1, gave the predicted amino acid sequence, but was missing the first 7 amino acids of the signal sequence at its 5' end, shown in SEQ ID NO:5. The second 5' cDNA clone, AlfAFP2, was highly homolgous to AlfAFP1. It contains a complete signal peptide coding sequence, shown in SEQ ID NO:6. Translation of the cDNA gave a truncated mature peptide of 39 amino acids shown in SEQ ID NO:14. A nucleotide sequence alignment of the two homologs, AlfAFP1 and AlfAFP2, is shown in FIG. 3.

The 3' region of the polypeptide cDNA was cloned as follows. First strand cDNA generated for 5' RACE was used as template for the amplification of the 3' portion of the polypeptide cDNA by PCR™ using the GeneAmp DNA Amplification Reagent Kit (Perkin Elmer Cetus) and the reaction conditions recommended by the manufacturer.

The two primers used for amplification were: 1) mixed oligonucleotide 34-mers (14 nucleotides for cloning sites and 20 nucleotides for gene specificity, degeneracy of 32, SEQ ID NO:7) made to amino acid positions 4 to 10 of the polypeptide sequence; and 2) an oligo-dT primer that aneals to the poly(A+) tail of the cDNA, SEQ ID NO:8. PCR™ reaction products were analyzed by agarose gel electrophoresis, and a single band of about 400 bp was present in the complete reaction mixture but not in the control reaction mixture that contained only one primer. This band was cut out of the gel and the DNA was isolated using an Ultrafree-MC centrifugation filter unit (Millipore). The DNA fragment was digested with BamHI, cloned into the plasmid pGEM11Zf(+) (Promega), and the insert sequenced on an 373 DNA Sequencer Stretch Model from Applied Biosystem using the PRISM Ready Reaction DyeDeoxy Terminator Cycle Sequencing Kit (Applied Biosystems). The sequence is shown in SEQ ID NO:9.

The 5' region (SEQ ID NO:5) and the 3' region (SEQ ID NO:9) of the polypeptide cDNA overlapped by 112 nucleotides. A full length polypeptide cDNA, as shown in SEQ ID NO:6, was formed by combining the following 3 sequence elements: nucleotides 1 to 112 of SEQ ID NO:6, nucleotides 20 to 198 of SEQ ID NO:5, and nucleotides 111 to 308 of SEQ ID NO:9.

As shown in FIG. 1, the antifungal polypeptide cDNA contains a 74 bp 5' leader sequence, a 219 bp open reading frame coding for a 72 amino acid polypeptide, and a 3' untranslated region of 179 bp up to the poly (A+) tail. The deduced polypeptide consists of a putative signal peptide of 27 amino acids and a mature polypeptide of 45 amino acids, which is identical to the sequence determined by mass spectrometry analysis and direct amino acid sequencing (see Examples 1 and 2) . The actual signal peptide cleavage occurs between alanine and arginine, i.e., at the arrow in FIG. 1.

For the convenience of cloning, restriction sites were engineered by PCR™ into the ends of the cDNA fragment that contained the coding region of the polypeptide cDNA. A 5' gene-specific primer containing 15 bp upstream of the start codon (ATG) and 39 bp of the prepolypeptide with a BamHI restriction site (SEQ ID NO:11) and a 3' gene-specific primer with a BamHI restriction site after the stop codon (TAA) (SEQ ID NO:12) were used to amplify the cDNA fragment from the cDNAs made by reverse transcription of mRNAs as described above. The PCR™ amplified fragment is shown in SEQ ID NO:13.

The PCR™ product was subcloned as a 241 bp BamHI fragment into the BamHI site of a previously constructed E. coli cassette vector pMON23317 (FIG. 4) containing an E35S promoter with a maize Hsp70 intron to create pMON22653 (FIG. 5). The 3' nontranslated polyadenylation sequence of the nos gene was also provided as the terminator. The vector also contained a multilinker site between the intron and the terminator sequences, NotI sites before and after the promoter and the terminator sequences, and an ampicillin resistance gene. The cDNA insert in pMON22653 was sequenced using a primer made to the sequence of the HSP70 intron 50 bp upstream of the BamHI cloning site The sequence of this cDNA insert is shown in SEQ ID NO:13, which is in the correct transcriptional orientation and its deduced amino acid sequence matches that of the polypeptide by direct amino acid sequence analysis (see SEQ ID:2).

5.5 EXAMPLE 5

5.5.1 Plasmids for Potato Transformation

The 263 bp BamHI/EcoRI fragment encoding AlfAFP1 was cloned from plasmid pMON22653 (FIG. 5) into previously constructed E. coli cassette vector pMON22575 (FIG. 6), replacing the p46 gene therein. The resulting plasmid, designated pMON22656 (FIG. 7), was cleaved with NotI to isolate the NotI fragment containing the polypeptide-encoding cDNA. This NotI fragment was subsequently inserted into the NotI site of pMON17227 (FIG. 8), a double border plant transformation vector. The resulting plasmid was designated pMON22659 (FIG. 9), and contains DNA fragments as follows: The bacterial spectinomycin/streptomycin resistance gene (Spc/Str) (Fling et al., 1985), followed by the right border of the T-DNA. Adjacent to the right border is the synthetic bacterial glyphosate resistance CP4 5-enolpyruvyl-3-phosphoshikimate synthase (EPSPS) gene driven by the FMV promoter (see PCT publication WO 92/04449). The CP4 gene confers glyphosate resistance to the transformants, and thus the capability of using glyphosate as the means for selecting transformants. A chloroplast transit peptide from the Arabidopsis 5-enopyruvyl-3-phosphoshikimate synthase gene(EPSPS) was fused to the CP4 gene to target the CP4-EPSPS protein to the chloroplasts. At the 3' end of the CP4 gene is the E9 3' end that provides a transcriptional termination site and polyadenylation signal sequence. The next chimeric segments consist of the FMV promoter, the antifungal polypeptide cDNA, and the nos 3' end. This is followed by the left border of the T-DNA, and the origin of replication (ori-322) (Stalker et al., 1981).

5.5.2 Triparental Mating Procedure

Prior to transformation, E. coli containing pMON22659 were mated with Agrobacterium ABI by a triparental mating procedure with E. coli harboring the helper plasmid pRK2013 (Ditta et al., 1980). ABI is the A208 Agrobacterium tumefaciensstrain carrying the disarmed pTiC58 plasmid pMP90RK (Koncz et al., 1986). The disarmed Ti plasmid provides the trfA gene functions that are required for autonomous replication of the pMON vectors after conjugation into the ABI strain. When plant tissue is incubated with the ABI::pMON conjugates, the vectors are transferred to the plant cells by the vir functions encoded by the disarmed pMP90RK Ti plasmid.

Agrobacterium were grown for 30 hours at 30° C. in LB medium (10 g tryptone, 5 g yeast extract, and 5 g NaCl per liter) containing 25 µg/ml chloramphenicol and 50 µg/ml kanamycin. E. coli containing pRK2013 were grown overnight in LB medium containing 50 µg/ml kanamycin. E. coli harboring pMON22659 were grown in LB medium containing 75 µg/ml spectinomycin. After all of the cultures were grown, 4 mls of LB medium were added to a tube containing 100 µl each of Agrobacterium ABI, E. coli/pRK2013, and E. coli/pMON22659. This mixture was centrifuged in a microfuge for 1 min., and the supernatant fraction decanted. The pellet fraction was resuspended in the remaining liquid (approximately 100 µl), and an aliquot (approximately 25 µl) was pipetted onto the center of an LB agar (1.5%) plate. After growth overnight at 30° C., an aliquot of cells from this plate was streaked onto an LB agar plate supplemented with 75 µg/ml spectinomycin, 50 µg/ml kanamycin, and 25 µg/ml chloramphenicol.

After 24–48 hours at 30° C., colonies were present on the plate streaked with cells resulting from the triparental mating of E. coli containing a pMON2659 plasmid, E. coli containing pRK2013, and Agrobacterium ABI, while no colonies were present on the control plate streaked with cells from the mating of the pMON22659-containing E. coli and ABI (without E. coli containing pRK2013, which is required for plasmid mobilization). After the triparental mating, 4 colonies were selected from the former plate, and each was separately inoculated into a liquid culture of LB supplemented with 75 µg/ml spectinomycin, 50 µg/ml kanamycin, and 25 µg/ml chloramphenicol, and grown at 30° C. The presence of the DNA encoding the different antifungal polypeptides was confirmed by restriction analysis of plasmid DNA isolated from the Agrobacterium cells. A culture containing DNA encoding AlfAFP1 was used for transformation of potato plants.

5.5.3 Transformation of Potato Plants

Agrobacterium containing pMON22659 were grown overnight in 2 mls of LB medium containing 75 µg/ml spectinomycin, 25 µg/ml chloramphenicol, and 50 µg/ml kanamycin, pH 7.0. The following day, the bacteria were diluted 1:10 with MSO medium containing 4.4 g MS salts (Sigma Chemical Co., St. Louis, Mo.), 30 g sucrose, and 2 mls vitamin B5 (Sigma catalogue # G 1019) in a 1 liter volume, pH 5.7, or until an optical density reading of 0.2–0.33 at 600 nm was obtained.

Leaves were removed from the stems of potato plants (Solanum tuberosum var. Russet Burbank) that had been grown from stem cuttings containing nodes under sterile conditions, including a temperature of 19° C., a 16 hr light/8 hr dark cycle, and a light intensity of 100 µE/sec/m$^2$, for three weeks on PM medium containing 4.4 g MS salts (Sigma Chemical Co., St. Louis, Mo.), 30 g sucrose, 0.17 g $NaH_2PO_4.H_2O$, 0.4 mg thiamine-HCl, 25 g ascorbic acid, and 0.1 g inositol per liter, pH 6.0, and 0.2% Gelrite agar. The stems were cut into 3–5 mm segments.

Before inoculation, 30 stem segments were placed onto a co-culture plate to serve as noninoculated controls. Co-culture plates contained 0.9% agar-solidified 1/10 MS salts (Murashige et al., 1962) and 3% sucrose, and were prepared by first coating the agar with 2 mls of 6–7 day old tobacco suspension cells as a feeder layer (Fraley et al., 1983), and then overlaying these cells with an 8.5 cm disc of sterile Whatman filter paper.

The explant segments to be transformed were inoculated by pouring the diluted bacterial suspension onto the stem pieces and allowing the mixture to incubate for 15 min. The bacterial suspension was then aspirated off the explant segments, which were subsequently spread evenly onto co-culture plates (about 90 stem pieces per plate). After a 2 day co-culture period at 19° C. under a 16 hr light/8 hr dark cycle and a light intensity of 100 µE/sec/m$^2$, the explants were placed onto 0.9% agar-solidified callus induction medium containing 1×MS salts, 5.0 mg/l zeatin riboside, 10 mg/l $AgNO_3$, 3% sucrose, 500 mg/l carbenicillin, and 0.1 mg/l napththaleneacetic acid, and incubated at 19° C. under a 16 hr light/8 hr dark cycle for 2 days. Explants were subsequently transferred onto callus induction medium supplemented with 0.025 mM glyphosate for selection. After 4 weeks, explants were placed onto 0.9% agar-solidified shoot induction medium containing 1×MS salts, 5.0 mg/l zeatin riboside, 10 mg/l $AgNO_3$, 3% sucrose, 500 mg/l carbenicillin, 0.3 mg/l GA3, and 0.025 mM glyphosate. Shoots began to appear at 8 weeks. Explants were transferred to fresh shoot induction medium every 4 weeks over a 12 week period. Shoots were excised from calli and placed on PM medium solidified with 0.2% Gelrite agar for about 2 weeks or until they developed roots and were large enough to be placed into soil. Once transplanted into Metro-Mix 350 (Hummert Seed Co., St. Louis), seedlings were grown in the greenhouse for 2–3 months under a 14 hr light/8 hr dark regime under a light intensity of 600–700 µE/sec/m$^2$, a day temperature of 65–75° F., a night temperature of 55–65° F., and a relative humidity of 60%.

5.5.4 Analysis of Antifungal Polypeptide Expression in Transgenic Potato Plants Leaf samples (20 to 100 mg) were taken from transgenic plants grown to 1 to 2 inches in height. The leaf samples were ground in PBST buffer (15 μ/mg tissue) containing 1 mM $KH_2PO_4$, 10 mM $Na_2HPO_4$, 137 mM NaCl, 2.7 mM KCl, pH 7.4, and 0.05% Tween-20, and allowed to sit at 4° C. overnight. After centrifugation, 100 μl of the supernatant was used in an ELISA assay. Polyclonal antibodies against AlfAFP polypeptide (SEQ ID NO:2) were prepared by Pocono Rabbit Farm (Canadensis, Pa.). Wells of a Nunc Maxi-sorp 96 well plate (Nunc #4-39454) were coated with antibodies against AlfAFP1 polypeptide by adding 100 μl of antibodies (1 mg IgG/ml) diluted 1:250 in coating buffer containing 1.59 g $Na_2CO_3$ and 2.93 g $NaHCO_3$ per liter distilled water, pH 9.6, and incubating at 4° C. overnight. The coating solution was then removed from the wells, which were then washed three times with PBST. One hundred μl of leaf supernatant or appropriately diluted polypeptide standards in PBST supplemented with 0.2% (w/v) BSA, fraction V (Sigma, St. Louis) were added to the wells.

The concentration of each polypeptide in extracts from transgenic plants was determined from standard curves constructed using varying amounts of the respective purified polypeptide. AlfAFP1 cross-reacted with the polyclonal antibody preparation. After overnight incubation at 4° C., the solutions were removed from the wells, and the wells were washed three times with PBST. One hundred μl of a 1:1000 dilution in PBST of a 0.5 mg/ml AlfAFP1 antibody/alkaline phosphatase conjugate prepared according to Boorsma et al. (1975) were added to each well. The plate was incubated at 22° C. for 4 hours, and the wells were then washed five times with PBST. One hundred μl of a freshly prepared solution of p-nitrophenyl phosphate (1 mg/ml) (Sigma Chemical Co., St. Louis, Mo.) dissolved in 200 mM Tris buffer, pH 9, were added to each well, and the plate was incubated at 22° C. for 1 hour. The optical density at 605 nm was determined using a Thermo-max microplate reader (Molecular Devices, Menlo Park, Calif.). Plants expressing different levels of antifungal polypeptides were used for subsequent disease tests.

5.5.5 Verticillium Wilt Control in Transgenic Plants

Conidia and mycelia of a 2–3 week old culture of virulent *Verticillium dahliae* were used to inoculate a PDA (potatoes, 200 g/l; Bacto dextrose, 20 g/l; and Bacto agar, 15 g/l) Petri plate. This culture was allowed to grow at 22° C. for 4–5 days. Conidia were then harvested by washing the culture plate with sterile distilled water and filtering the liquid through two layers of cheesecloth. The conidial spore concentration was determined using a hemacytometer, and adjusted to $1 \times 10^6$ conidia/ml with sterile distilled water.

Transgenic and non-transgenic potato plants were grown from stem cuttings under sterile conditions as described above in plastic cups containing 50 mls of PM-agar medium. When plants were about 1–2 inches tall, they were removed from the medium and their roots were dipped in the spore suspension (Joaquim et al., 1991). The inoculated plants were then transplanted into 6-inch pots containing Metro-Mix 350 soil. After transplanting, each plant received an additional 5 mls of the spore suspension ($1 \times 10^6$ condida/ml) on the soil surface around the base of the stem. The pots were placed in a growth chamber under the following conditions: temperature at 20° C., light intensity at 320 μE/sec/cm², 12 hr day/12 hr night light cycle, subirrigation with water 2 times/day, 20 minutes soaking each time. Four weeks after inoculation, the plants were scored for disease severity on a scale of 0–100% (Horsfall et al., 1945). To develop a disease progress curve over time, plants were rated once a week for at least 8 weeks.

5.5.6 Verticillium Wilt Resistance in AlfAFP-Expressing Potato Plants

Twenty-one independent transgenic potato lines expressing AlfAFP1 were tested for resistance to Verticillium wilt disease. The expression of AlfAFP1 in leaves is an indicator of the expression in the whole plant since the FMV promoter used to drive expression of the respective encoding DNAs directs gene expression constitutively in all tissue types of potato plants. Twenty one independent lines of non-expressors of AlfAFP that were identified during AlfAFP expression analysis were included in the disease test as negative controls. In the test, 18 independent vector control lines were also included as negative controls. These were generated from transformations employing Agrobacterium harboring plasmid pMON17227 (vector control; FIG. 8), which does not contain any antifungal polypeptide-encoding DNA.

Table 2 summarizes the qualitative protein expression data for each of the lines, and the disease severity rating of each individual line in the Verticillium wilt disease test determined at 46 days post inoculation. For convenience, the same disease data are also presented as a bar graph in FIG. 10. The order of appearance of each potato line in Table 2 (from top to bottom) and in FIG. 10 (from left to right) is the same.

TABLE 2

Expression of AlfAFP1 and *Verticillium* Wilt Resistance in Transgenic Potato Plants

| Plants | Line # | Protein Expression (qualitative ELISA) | Disease Severity (%) (46 Days Post Inoc.) |
|---|---|---|---|
| AlfAFP1 positive plants | 17562 | + | 5 |
| | 17554 | + | 17.5 |
| | 17556 | + | 20 |
| | 17557 | + | 22.5 |
| | 17563 | + | 25 |
| | 17570 | + | 27.5 |
| | 17566 | + | 30 |
| | 17567 | + | 35 |
| | 17550 | + | 40 |
| | 17551 | + | 45 |
| | 18945 | + | 50 |
| | 18968 | + | 50 |
| | 18944 | + | 45 |
| | 17652 | + | 35 |
| | 18940 | + | 35 |
| | 17564 | + | 30 |
| | 17568 | + | 25 |
| | 17645 | + | 25 |
| | 17561 | + | 22.5 |
| | 17558 | + | 20 |
| | 17636 | + | 17.5 |
| | | Average | 29.6 |
| AlfAFP1 negative plants | 17638 | − | 22.5 |
| | 18946 | − | 37.5 |
| | 17642 | − | 45 |
| | 17555 | − | 50 |

TABLE 2-continued

Expression of AlfAFP1 and
Verticillium Wilt Resistance in Transgenic Potato Plants

| Plants | Line # | Protein Expression (qualitative ELISA) | Disease Severity (%) (46 Days Post Inoc.) |
|---|---|---|---|
|  | 18971 | – | 60 |
|  | 17643 | – | 65 |
|  | 17655 | – | 70 |
|  | 17637 | – | 72.5 |
|  | 17646 | – | 75 |
|  | 18955 | – | 80 |
|  | 18950 | – | 100 |
|  | 18958 | – | 100 |
|  | 17552 | – | 80 |
|  | 18975 | – | 75 |
|  | 18963 | – | 70 |
|  | 18972 | – | 70 |
|  | 18952 | – | 65 |
|  | 18956 | – | 60 |
|  | 18974 | – | 45 |
|  | 18943 | – | 40 |
|  | 17648 | – | 35 |
|  |  | Average | 62.7 |
| Vector control | 14947 | 0 | 30 |
|  | 14924 | 0 | 40 |
|  | 14925 | 0 | 40 |
|  | 14918 | 0 | 50 |
|  | 14926 | 0 | 50 |
|  | 14928 | 0 | 50 |
|  | 14936 | 0 | 75 |
|  | 14920 | 0 | 100 |
|  | 14923 | 0 | 100 |
|  | 14927 | 0 | 100 |
|  | 14935 | 0 | 100 |
|  | 14941 | 0 | 95 |
|  | 14933 | 0 | 60 |
|  | 14930 | 0 | 50 |
|  | 14931 | 0 | 50 |
|  | 14940 | 0 | 50 |
|  | 14946 | 0 | 40 |
|  | 14949 | 0 | 40 |
|  |  | Average | 62.2 |

As shown in Table 2 and FIG. 10, disease severity on the AlfAFP1 expressing plants averaged 52% less than that of the non-expressors or the vector controls. This was calculated as follows: [(average of 18 vector control lines)–(average of 21 lines of expressors)]×100%/(average of 18 vector control lines); or [(average of 21 lines of non-expressors)–(average of 21 lines of expressors)]×100%/(average of 21 lines of non-expressors). Thirteen out of 21 lines of AlfAFP1 expressing lines had disease severity rated equal to or less than 30%; in contrast, only 1 out of 21 non-expressing or 1 out of 18 vector control lines had a disease severity rated less than 30%. These results demonstrate that AlfAFP1 confers Verticillium wilt resistance to potato plants expressing this protein. The invention being thus described, it is obvious that the same can be varied in many ways. Such variations are not to be regarded as a departure from the spirit and scope of the present invention, and all such modifications as would be obvious to one skilled in the art are intended to be included within the scope of the following claims

6.0 REFERENCES

U.S. Pat. No. 4,940,840,
PCT International Publication No. WO 93/05153
PCT International Publication No. WO 93/05153.
PCT International Publication No. WO 92/04449.
PCT International Publication No. WO 88/00976
PCT International Publication No. WO 90/07001
PCT International Publication No. WO 91/06312
PCT International Publication No. WO 91/18984
European Patent Application 0 392 225
European Patent Application 0 307 841
European Patent Application 0 332 104
European Patent Application 0 440 304
European Patent Application 0 418 695
European Patent Application 0 448 511
European Patent Application 0 392 225.
European Patent Application 0 292 435
European Patent Application 0 290 123
Ausubel et al., Current Protocols in Molecular Biology, John Wiley and Sons, Inc., 1995.
Bauer et al., Gene, 37:73, 1985.
Becker et al., Plant J., 5:299, 1994.
Bent et al., Science, 265:1856–1860, 1994.
Bol et al., Ann. Rev. Phytophathol, 28:113–138, 1990.
Boorsma et al., J. Histochem. Cytochem., 23:200–207, 1975.
Bower and Birch, Plant J., 2:409, 1992.
Bowles, Ann. Rev. Biochem, 59:873–907, 1990.
Brears et al., Agro-Food-Industry Hi-Tech., 10–13, 1994.
Broekaert et al., Plant Physiol., 108:1353–1358, 1995.
Bytebier et al., Proc. Natl. Acad. Sci. U.S.A., 84:5345, 1987.
Campbell et al., Plant Physiol., 92:1–11, 1990.
Cassas et al., Proc. Natl. Acad. Sci. U.S.A., 90:11212, 1993.
Celano et al., Biotechniques, 15:27–28, 1993.
Chiang et al., Molecular Plant-Microbe Interactions, 4:324–331, 1991.
Christensen et al., Plant Mol. Biol., 18:675,689, 1992.
Christou et al., Bio/Technology, 9:957, 1991.
Christou, Agro Food Industry Hi Tech, 17, 1994.
Compton T., In: PCR™ Protocols, A Guide to Methods and Applications, Innis et al., Eds., Academic Press, San Diego, 39–45, 1990.
Craik, BioTechniques, 3:12–19, 1985.
Cuypers et al, Mol. Plant-Microbe Interact, 1:157–160, 1988.
De la Pena et al., Nature, 325:274, 1987.
Ditta et al., Proc. Natl. Acad. Sci. U.S.A., 77:7347, 1980.
Ellis et al., Proc. Natl. Acad. Sci. U.S.A., 92:4185, 1995.
Fischoff et al., European Patent Application 0 385 962.
Fisk and Dandekar, Scientia Horticulturae, 55:5–36, 1993.
Fling et al., Nucl. Acids Res., 13:7095–7106, 1985.
Fraley et al., Proc. Natl. Acad. Sci. U.S.A., 80:4803, 1983.
Frits Eckstein et al., Nucleic Acids Research, 10:6487–6497, 1982.
Fritzemeier et al., Plant Physiol., 85:34–41, 1987.
Fromm et al., BiolTechnology, 8:833, 1990.
Gasser and Fraley, Science, 244:1293, 1989.
Gordon-Kamm et al., Plant Cell, 2:603, 1990.
Grant et al., Science, 269:843–846, 1995.
Horn et al., Plant Cell Rep., 7:469, 1988.
Horsfall et al., Phytopathology, 35:655, 1945.
Joaquim et al., Phytopathology, 81:552–558, 1991.
Jones et al., Science, 266:789–793, 1994.
Kawasaki E. S., In: PCR™ Protocols, A Guide to Methods and Applications, Innis et al., Eds., Academic Press, San Diego, 21–27, 1990.
Kay et al., Science, 236:1299, 1987.
Koncz et al., Mol. Gen. Genet., 204:383–396, 1986.
Koziel et al., Bio/Technology, 11:194, 1993.
Laemmli, Nature, 227:680–685, 1970.
Leon et al., Proc. Natl. Acad. Sci. U.S.A., 92:10413–10417, 1995.

Linthorst, *Crit. Rev. Plant Sci.*, 10:123–150, 1991.
Logemann et al., *Plant Cell*, 1:151–158, 1989.
Luo and Wu, *Plant Mol. Biol. Rep.*, 6:165, 1988.
Mandel et al., *Plant Mol. Biol*, 29:995–1004, 1995.
Martens K., *Spray Drying Handbook*, Third Edition, G. Goodwin, Ltd., London, 1979.
Martini et al., *Mol. Gen. Genet.*, 263:179, 1993.
Matton et al., *Mol. Plant-Microbe Interact*, 2:325–331, 1989.
McElroy etal., *Plant Cell*, 2:163–171, 1990.
Murashige et al., *Physiol. Plant.*, 15:473, 1962.
Murray et al., *Nucl. Acids. Res.*, 17:477–498, 1989.
Osuna et al., *Critical Reviews In Microbiology*, 20:107–116, 1994.
Pyee et al., *Plant J.*, 7:49–59, 1995.
Rhodes et al., *Science*, 240:204, 1988.
Samac et al., *Plant Cell*, 3:1063–1072, 1991.
Sambrook et al., *Molecular Cloning: A Laboratory Manual*, Cold Spring Harbor Press, Cold Spring Harbor, N.Y., 1989.
Sambrook et al., *Molecular Cloning: A Laboratory Manual*, Second Edition, Cold Spring Harbor Laboratory Press, Cold Spring Harbor, N.Y., 1989.
Schroder et al., *Plant J.*, 2:161–172, 1992.
Scoble et al., *A Practical Guide to Protein and Peptide Purification for Microsequencing*, P. Matsudaira, Ed., Academic Press, Inc., San Diego, 125–153, 1993.
Smith et al, In: *Genetic Engineering: Principles and Methods*, Setlow et al., Eds., Plenum Press, N.Y., 1–32, 1981.
Somers et al., *Bio/Technology*, 10:1589, 1992.
Song et al., *Science*, 270:1804–1806, 1995.
Stalker et al., *Mol. Gen. Genet.*, 181:8–12, 1981.
Stone et al., *A Practical Guide to Protein and Peptide Purification for Microsequencing*, P. Matsudaira, Ed., Academic Press, Inc., San Francisco, 55–56, 1993.
Terras et al., *J. Biol. Chem.*, 267:15301–15309, 1992.
Toriyama et al., *Bio/Technology*, 6:10, 1988.
Troy Weeks et al., *Plant Physiol.*, 102:1077, 1993.
Van Den Ackerveken et al., *Plant J.*, 2:359, 1992.
van Falkenberg, *Pesticide Formulations*, Second Edition, Marcel Dekker, N.Y., 1972–1973.
Vasil et al., *Bio/Technology*, 10:667, 1992.
Walder et al., *Gene*, 42:133, 1986.
Wan and Lemaux, *Plant Physiol.*, 104:37, 1994.
Wang et al., *Bio/Technology*, 10:691, 1992.
Watkins, *Handbook of Insecticide Dust Diluents and Carriers*, Second Edition, Darland Books, Caldwell, N.J.
Weigel, *Annu. Rev. Genetics*, 29:19–39, 1995.
Whitham et al., *Cell*, 78:1101–1115, 1994.
Winnacker-Kuchler, *Chemical Technology*, Fourth Edition, Volume 7, Hanser Verlag, Munich, 1986.
Winter, *Mol. Gen. Genet.*, 221:315–319, 1988.
Worthington and Walker, *The Pesticide Manual*, Seventh Edition, British Crop Protection Council, 1983.
Zhang and Wu, *Theor. Appl. Genet.*, 76:835, 1988.
Zhang et al., Plant Cell Rep., 7:379, 1988.Zhong et al., Plant Cell Rep., 13:1, 1993.

What is claimed is:

1. An isolated antifungal polypeptide encoded by a DNA molecule, either isolated from a natural source or synthesized, said DNA molecule comprising a nucleotide sequence selected from the group consisting of:
   a) the nucleotide sequence of FIG. 1 (SEQ ID NO:10 from position 18 to 507);
   b) the nucleotide sequence of SEQ ID NO:13;
   c) the nucleotide sequence of SEQ ID NO:13 from position 105 to 239; and
   d) a nucleotide sequence that encodes the same peptide as that encoded by the nucleotide sequence of a), b) or c).

2. The polypeptide according to claim 1 comprising the amino acid sequence of SEQ ID NO:2 or SEQ ID NO:14.

3. The polypeptide of claim 1 wherein said polypeptide is isolated from *Medicago alfalfa*.

4. An isolated antifungal polypeptide comprising the amino acid sequence of SEQ ID NO:2 or SEQ ID NO:14.

5. A composition comprising an antifungally effective amount of the polypeptide of claim 1 in a suitable solvent.

6. A method of controlling plant fungus, comprising providing to a plant an antifungally effective amount of the polypeptide of claim 1.

7. The method of claim 6 wherein the polypeptide is provided by the composition of claim 5.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 43 amino acids
        (B) TYPE: amino acid
        (C) STRANDEDNESS:
        (D) TOPOLOGY: linear (xi) SEQUENCE DESCRIPTION: SEQ ID NO:1:

```
Arg Thr Cys Glu Asn Leu Ala Asp Lys Tyr Arg Gly Pro Cys Phe Ser
1               5                   10                  15

Gly Cys Asp Thr His Cys Thr Thr Lys Glu Asn Ala Val Ser Gly Arg
            20                  25                  30

Cys Arg Asp Asp Phe Arg Cys Xaa Xaa Thr Lys
        35                  40
```

(2) INFORMATION FOR SEQ ID NO:2:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:2:

```
Arg Thr Cys Glu Asn Leu Ala Asp Lys Tyr Arg Gly Pro Cys Phe Ser
1               5                   10                  15
```

```
Gly Cys Asp Thr His Cys Thr Thr Lys Glu Asn Ala Val Ser Gly Arg
         20                  25                  30

Cys Arg Asp Asp Phe Arg Cys Trp Cys Thr Lys Arg Cys
         35                  40                  45
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(16, 22)
        (D) OTHER INFORMATION: /mod_base= OTHER
            /note= "N = inosine"

(ix) FEATURE:
        (A) NAME/KEY: modified_base
        (B) LOCATION: one-of(19, 25, 28, 31)
        (D) OTHER INFORMATION: /mod_base= OTHER
            /note= "D = A or G or T"

(ix) FEATURE:
        (A) NAME/KEY: modified_base
        (B) LOCATION: 24
        (D) OTHER INFORMATION: /mod_base= OTHER
            /note= "K = G or T"

(xi) SEQUENCE DESCRIPTION: SEQ ID NO:3:

```
GGGAATTCGG ATCCANCADC ANCKDAADTC DTC                               33
```

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: join(18..19, 23..24, 28..29)
        (D) OTHER INFORMATION: /mod_base= OTHER
            /note= "N = inosine"

(xi) SEQUENCE DESCRIPTION: SEQ ID NO:4:

```
GGGAATTCGG ATCCGGGNNG GGNNGGGNNG                                   30
```

(2) INFORMATION FOR SEQ ID NO:5:

(i) SEQUENCE CHARACTERISTICS:
        (A) LENGTH: 200 base pairs
        (B) TYPE: nucleic acid
        (C) STRANDEDNESS: double
        (D) TOPOLOGY: linear (ix) FEATURE:
        (A) NAME/KEY: modified_base
        (B) LOCATION: 17
        (D) OTHER INFORMATION: /mod_base= OTHER
            /note= "N = A or C or G or T"

(xi) SEQUENCE DESCRIPTION: SEQ ID NO:5:

```
GGGGGGGGGG GGGGGGNCAG GCTTATGCTT CCTCTTCTTG GTTCTCTTTG TTGCACAAGA    60

AATTGTGGTG ACAGAAGCCA GAACATGTGA GAATTTGGCA GATAAATATA GGGGACCATG   120

CTTTAGTGGT TGTGACACTC ACTGCACAAC CAAAGAGAAC GCAGTTAGTG AAGGTGTAG    180
```

GGACGACTTC CGCTGCTGCT                                                    200

(2) INFORMATION FOR SEQ ID NO:6:

(i) SEQUENCE CHARACTERISTICS:
        (A) LENGTH: 293 base pairs
        (B) TYPE: nucleic acid
        (C) STRANDEDNESS: double
        (D) TOPOLOGY: linear (ix) FEATURE:
        (A) NAME/KEY: modified_base
        (B) LOCATION: one-of(17, 265)
        (D) OTHER INFORMATION: /mod_base= OTHER
            /note= "N = A or C or G or T"

(xi) SEQUENCE DESCRIPTION: SEQ ID NO:6:

GGGGGGGGGG GGGGGGNTGT CAAACACACA CATAACACAT AAGTGACCGT GAGTCATTAA         60

ATTTATATAT ATTCATCAAT CTAATCAAAC TATGGAGAAG AAATCACTAG CTGGCTTATG        120

CTTCCTCTTC CTCGTTCTCT TGTTGAACA AGAAATTATG GTGACCGAGG CAGCTACTTG         180

TGAGAATTTG GCTAACACAT ACAGGGGACC ATGCTTCGGT GGTTGTGACT TTCACTGCAA        240

AACCAAAGAA CACTTACTTA GCGGNAGGTG CAGGGACGAC TTCCGCTGCT GCT              293

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: one-of(17, 31)
        (D) OTHER INFORMATION: /mod_base= OTHER
            /note= "D = A or G or T"

(ix) FEATURE:
        (A) NAME/KEY: modified_base
        (B) LOCATION: one-of(19, 20, 28)
        (D) OTHER INFORMATION: /mod_base= OTHER
            /note= "B = C or G or T"

(ix) FEATURE:
        (A) NAME/KEY: modified_base
        (B) LOCATION: one-of(22, 25)
        (D) OTHER INFORMATION: /mod_base= OTHER
            /note= "N = inosine"

(xi) SEQUENCE DESCRIPTION: SEQ ID NO:7:

GGGAATTCGG ATCCGADABB TNGCNGABAA DTA                                     33

(2) INFORMATION FOR SEQ ID NO:8:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:8:

GGGAATTCGG ATCCTTTTTT TTTTTTTTTT TT                                      32

(2) INFORMATION FOR SEQ ID NO:9:

(i) SEQUENCE CHARACTERISTICS:
        (A) LENGTH: 327 base pairs (B) TYPE: nucleic acid
        (C) STRANDEDNESS: double
        (D) TOPOLOGY: linear (ix) FEATURE:
        (A) NAME/KEY: modified_base
        (B) LOCATION: one-of(244, 305)
        (D) OTHER INFORMATION: /mod_base= OTHER
            /note= "N = A or C or G or T"

(xi) SEQUENCE DESCRIPTION: SEQ ID NO:9:

```
GAGAATTTGG CGGATAAGTA TAGGGGACCA TGCTTTAGTG GTTGTGACAC TCACTGCACA      60

ACCAAAGAGA ACGCAGTTAG TGGAAGGTGT AGGGATGACT TTCGTTGTTA GTGTACTAAA     120

AGATGTTAAA TGGATCTCCT CCAACATCAA GATGTGCATG GAATAGTCTT TATAATAAAA     180

CTAAATAAAT AAAATGCACG CAGTATAGCT ACAACTTCAT CTATATATAT GTACTCAATA     240

TCGNGCATAA CGTATTAGTT ATGCACTTCT ATCATATGGA ATAAACATCA ATAAGTAATT     300

TCGTNTCCAA AAAAAAAAAA AAAAAAA                                         327
```

(2) INFORMATION FOR SEQ ID NO:10:

(i) SEQUENCE CHARACTERISTICS:
        (A) LENGTH: 507 base pairs
        (B) TYPE: nucleic acid
        (C) STRANDEDNESS: double
        (D) TOPOLOGY: linear (ix) FEATURE:
        (A) NAME/KEY: modified_base
        (B) LOCATION: one-of(17, 424, 485)
        (D) OTHER INFORMATION: /mod_base= OTHER
            /note= "N = A or C or G or T"

(xi) SEQUENCE DESCRIPTION: SEQ ID NO:10:

```
GGGGGGGGGG GGGGGGNTGT CAAACACACA CATAACACAT AAGTGACCGT GAGTCATTAA      60

ATTTATATAT ATTCATCAAT CTAATCAAAC TATGGAGAAG AAATCACTAG CTGGCTTATG     120

CTTCCTCTTC TTGGTTCTCT TTGTTGCACA AGAAATTGTG GTGACAGAAG CCAGAACATG     180

TGAGAATTTG GCAGATAAAT ATAGGGGACC ATGCTTTAGT GGTTGTGACA CTCACTGCAC     240

AACCAAAGAG AACGCAGTTA GTGGAAGGTG TAGGGACGAC TTCCGCTGCT GGTGTACTAA     300

AAGATGTTAA ATGGATCTCC TCCAACATCA AGATGTGCAT GGAATAGTCT TTATAATAAA     360

ACTAAATAAA TAAAATGCAC GCAGTATAGC TACAACTTCA TCTATATATA TGACTCAATA     420

TCGNGCATAA CGTATTAGTT ATGCACTTCT ATCATATGGA ATAAACATCA ATAAGTAATT     480

TCGTNTCCAA AAAAAAAAAA AAAAAAA                                         507
```

(2) INFORMATION FOR SEQ ID NO:11:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:11:

```
GGGGATCCCA ATCTAATCAA ACTATGGAGA AGAAATCACT AGCTGGCTTA TGCTTCCTCT      60

TC                                                                     62
```

(2) INFORMATION FOR SEQ ID NO:12:

(i) SEQUENCE CHARACTERISTICS:
        (A) LENGTH: 47 base pairs

```
            (B) TYPE: nucleic acid
            (C) STRANDEDNESS: single
            (D) TOPOLOGY: linear (xi) SEQUENCE DESCRIPTION: SEQ ID NO:12:

GGGGATCCTT AACATCTTTT AGTACACCAG CAGCGGAAGT CGTCCCT              47

(2) INFORMATION FOR SEQ ID NO:13:

(i) SEQUENCE CHARACTERISTICS:
            (A) LENGTH: 250 base pairs
            (B) TYPE: nucleic acid
            (C) STRANDEDNESS: double
            (D) TOPOLOGY: linear (xi) SEQUENCE DESCRIPTION: SEQ ID NO:13:

GGGGATCCCA ATCTAATCAA ACTATGGAGA AGAAATCACT AGCTGGCTTA TGCTTCCTCT    60

TCTTGGTTCT CTTTGTTGCA CAAGAAATTG TGGTGACAGA AGCCAGAACA TGTGAGAATT   120

TGGCAGATAA ATATAGGGGA CCATGCTTTA GTGGTTGTGA CACTCACTGC ACAACCAAAG   180

AGAACGCAGT TAGTGGAAGG TGTAGGGACG ACTTCCGCTG CTGGTGTACT AAAAGATGTT   240

AAGGATCCCC                                                         250

(2) INFORMATION FOR SEQ ID NO:14:

(i) SEQUENCE CHARACTERISTICS:
            (A) LENGTH: 39 amino acids
            (B) TYPE: amino acid
            (C) STRANDEDNESS:
            (D) TOPOLOGY: linear (xi) SEQUENCE DESCRIPTION: SEQ ID NO:14:

Ala Thr Cys Glu Asn Leu Ala Asn Thr Tyr Arg Gly Pro Cys Phe Gly
1               5                   10                  15

Gly Cys Asp Phe His Cys Lys Thr Lys Glu His Leu Leu Ser Gly Arg
            20                  25                  30

Cys Arg Asp Asp Phe Arg Cys
            35
```